(12) United States Patent
Tsuzuki et al.

(10) Patent No.: US 7,358,082 B2
(45) Date of Patent: Apr. 15, 2008

(54) DEVICE AND METHOD FOR CULTURING CELLS

(75) Inventors: Hirohiko Tsuzuki, Kanagawa (JP); Satoru Toda, Kanagawa (JP); Yasunori Ichikawa, Kanagawa (JP); Tetsuo Kurahashi, Kanagawa (JP); Fumiko Shiraishi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 641 days.

(21) Appl. No.: 10/891,477

(22) Filed: Jul. 15, 2004

(65) Prior Publication Data
US 2005/0042745 A1 Feb. 24, 2005

(30) Foreign Application Priority Data

| Jul. 16, 2003 | (JP) | ............................. 2003-275373 |
| Dec. 12, 2003 | (JP) | ............................. 2003-415266 |
| Dec. 12, 2003 | (JP) | ............................. 2003-415267 |
| Dec. 12, 2003 | (JP) | ............................. 2003-415268 |

(51) Int. Cl.
- *C12M 1/00* (2006.01)
- *C12M 1/12* (2006.01)
- *C12M 1/36* (2006.01)
- *C12N 5/00* (2006.01)
- *C12M 1/38* (2006.01)
- *C12M 3/00* (2006.01)
- *C12N 5/02* (2006.01)

(52) U.S. Cl. ............................. 435/293.1; 435/295.3; 435/286; 435/297.1; 435/297.2; 435/404

(58) Field of Classification Search ............. 435/293.1, 435/295.3, 404, 286, 297.1, 297.2
See application file for complete search history.

(56) References Cited

U.S. PATENT DOCUMENTS

| 5,376,548 A | * | 12/1994 | Matsuo et al. ............ 435/297.2 |
| 5,437,998 A | * | 8/1995 | Schwarz et al. ......... 435/298.2 |
| 6,468,792 B1 | * | 10/2002 | Bader ......................... 435/325 |
| 6,821,107 B1 | * | 11/2004 | Hara et al. .................. 425/397 |
| 2004/0072338 A1 | * | 4/2004 | Tsuzuki et al. .......... 435/289.1 |

FOREIGN PATENT DOCUMENTS

| EP | 0112155 | * | 6/1984 |
| GB | WO 88/08448 | * | 11/1998 |

OTHER PUBLICATIONS

Zeng Xianfang and Ruckenstein Eli. Supported chitosan-dye affinity membranes and theirprotein adsoption. Journal of Membrane Science.1996.v.117: 271-278.*

* cited by examiner

*Primary Examiner*—Walter D. Griffin
*Assistant Examiner*—Simon Vainberg
(74) *Attorney, Agent, or Firm*—Sughrue Mion, PLLC

(57) ABSTRACT

An object of the present invention is to construct a culture device optimized for culturing animal cells. The present invention provides a device for culturing cells which comprises at least one water-containing polymer gel film for adhering animal cells onto at least one surface of the film, and has a structure capable of supplying different liquids to both sides of the film.

12 Claims, 6 Drawing Sheets

DEVICE AND METHOD FOR CULTURING CELLS

FIELD OF THE INVENTION

The present invention relates to a cell culture technology. More specifically, the present invention relates to a device for culturing cells, a method of culturing animal cells using the device, and cultured animal cells obtained by the method.

BACKGROUND ART

In research and development of medicaments, experimental animals have been used for a long time. On the other hand, it is sometimes difficult to find the efficacy and side effects of medicaments on the basis of data of experimental animals due to intrinsic metabolic functions specific to humans. Also, reduction of experimental animals is recently suggested from the viewpoint of an animal protection. In addition, high cost is incurred for clinical trials in humans. For these reasons, it is desired to reproduce artificial organs, in vitro, having the same function as living organs. Recently, regeneration medical techniques have been evolved, and thus construction of such a model has become possible.

An organ exhibits its functions within the living body when it is exposed to various fluids including blood. In order to construct a model of an organ, cell culturing must be performed in a flow system. Therefore, culturing methods using various reactors are proposed (JP Patent Publication (Kokai) No. 2001-190270 and U.S. Pat. No. 5,202,254).

In the living body, the fluid flows through a capillary to supply various substances to cells, and receive waste matters therefrom. On the other hand, for cells such as vascular endothelial cells which are directly exposed to the fluid (blood), the cells are stimulated by blood flow shearing. In order to establish culturing conditions which satisfy these requirements, cell culture in a microreactor is considered suitable for modeling of living system, and many studies have been conducted on this subject (Manabu Tokeshi et al. Anal. Chem., 74, 1565(2002); Shuichi Takayama et al., Proc. Natl. Acad. Sci. USA. 96, 5545 (1999); and M. J. Powers et al, Tissue Eng., 8, 499 (2002)).

In particular, when the liver is simulated as a model, culturing must be performed in the conditions which allow migration of substances between two culture mediums (corresponding to bile and blood) and the cells, while preventing a backward flow from the bile corresponding medium to the blood corresponding medium. A liver simulation model made from such a viewpoint is prepared by a method in which a flow is established from a blood-corresponding medium to a bile-corresponding medium and cells are cultured in the flow. However, the blood cannot be in direct contact with each other. In this respect, the aforementioned liver simulation model is not considered perfect.

There is a proposed method in which cells are cultured in two types of mediums with a diaphragm between them, practical in a bioreactor using a filamentous fungus for substance production (JP Patent Publication (Kokai) Nos. 7-322874 and 8-9958). However, these methods are not suitable for culturing animal cells and constructing a living-organ simulation model, since it is difficult to stimulate a blood flow and stimulate cells by blood flow shearing. Furthermore, as the feature of the cell culture device mentioned above, it is necessary to culture cells in a flow system for hours to days depending upon the purpose of culturing, and it is required to construct an equipment system enabling long and stable tests. In addition, it is also necessary to reduce the examination time by finding accelerating conditions, and to determine the counter-power of a sample by performing a compulsive test.

DISCLOSURE OF THE INVENTION

It is an object of the present invention to construct a culture device optimized for culturing animal cells. Thus, it is an object of the present invention to provide a cell culture device capable of culturing animal cells by supplying different types of flowing media to both surfaces of a culture, capable of simulating blood shearing and substance supply in a medium in contact with the animal cells, and capable of culturing the animal cells while preventing release of cell layers under a condition which is similar with that in a living body. More specifically, it is an object of the present invention to provide a device and method for culturing cells, capable of (1) supplying a substance uniformly to the cells to be cultured; (2) establishing a uniform flow for supplying a substance; (3) eliminating a dead space; and (4) preventing release of cell layers by the flow. Still more specifically, it is an object of the present invention to provide a cell culture device equipped with a control mechanism for establishing a uniform inner pressure in the system.

In the culturing of cells, a liquid must be supplied for quite a long time and thus it is difficult to use a one-way liquid supply means such as a micro syringe. Instead, a plurality of microsyringes which are alternately operated, a microgear pump, or multiple-head microplunger pump are used. However, these methods have problems that flow-rate and pressure may change at the time of switching. Thus, it is an object of the present invention to provide a device for culturing cells which eliminates these problems. Thus, it is an object of the present invention to reduce pulsation generated in a steady operation when a relatively compact and convenient pump-system is employed in the device, and to reduce variation in the flow-rate taking place when an alternately drived pump such as a multi-head plunger pump is used while switching heads alternately.

In addition to the basic functions as mentioned above, (5) reduction of test time and (6) evaluation of a test sample for adaptability to conditions, are required. The means for solving such requirements include control of temperature. So, it is an object of the present invention to realize a method of controlling temperature suitable for a cell culture device at a practical level.

As the features of the aforementioned cell culture device, it is necessary to culture cells in a flow system for hours to days depending on its purpose, and it is required to construct an equipment system enabling a long and stable tests.

The present inventors have intensively studied with a view to attaining the aforementioned objects. As a result, they found that the objects can be attained by using a bioreactor in which a water-containing polymer gel film is used as a carrier for adhering animal cells thereto, and which has a structure capable of supplying different fluids to one and the other sides of the water-containing polymer gel film respectively. Furthermore, they found that the aforementioned objects can be attained by providing, in the system for culturing desired cells by supplying a culture solution to a culturing device, pocket structure for establishing a uniform dynamic pressure of the culture solution across the width while it is introduced through an inlet pipe, so as to establish a uniform flow rate at sites across the width perpendicular to the flowing direction of the solution, flow channel for supplying the culture solution to a cell culture section having a uniform width, with the gap in the height direction within the range of 10 to 900 µm, and another pocket structure immediately upstream of an outlet pipe in order to suppress the effect of the flow toward the outlet.

They further found that the aforementioned objects can be attained by controlling culture conditions by controlling the pressure of a fluid flowing through the pocket portions or the flow channel to be at a predetermined value. The problem to be solved by the present invention is how stably a fluid is supplied to the cell culture section in the system constructed as mentioned above. The present invention is therefore directed to realize flow-rate control performed by faithfully following the program when a fluid is supplied in accordance with a predetermined program.

Furthermore, they also found that the aforementioned objects can be attained by providing, in the system for culturing desired cells by supplying a culture solution to a culture device, temperature controlling means near a flow channel at three or more sites including a site of cell culture section and sites upstream and downstream thereof so as to independently control the temperatures; and heat insulating means between respective two temperature controlling means such that the temperatures of temperature controlling means do not affect each other.

Moreover, they found that the aforementioned objects can be attained by providing, in a device for culturing cells adhered to a water-containing polymer gel film by supplying a culture solution, liquid pressurizing means for pressurizing a liquid to be supplied to the culture device, and flow rate measuring means for measuring the flow rate of a liquid so as to supply the liquid to the culture device in a predetermined amount.

Namely, the present provides a device for culturing cells which comprises at least one water-containing polymer gel film for adhering animal cells onto at least one surface of the film, and has a structure capable of supplying different liquids to both sides of the film.

Preferably, flow channels are provided on one and the other sides of the water-containing polymer gel film in such a way that different liquids can be flowed to one and the other sides of the film.

Preferably, the device of the present invention comprises at least one water-containing polymer gel film for adhering animal cells onto at least one surface of the film, flow channels provided on one and the other sides of the water-containing polymer gel film in such a way that different liquids can be flowed to one and the other sides of the film, and a means for holding the water-containing polymer gel film between the flow channels.

Preferably, one of the surfaces of the water-containing polymer gel film is covered with an animal cell adhesive material.

Preferably, the flow shearing force applied to the cells is 2.0 dyn/cm$^2$ or more.

Preferably, each of the flow channels is formed of the water-containing polymer gel film and an inner wall of the reactor, and the spacing between the water-containing polymer gel film and the inner wall of the reactor falls within 10 µm to 2 mm, both inclusive.

Preferably, 90% to 100% region, both inclusive, of the surface of the water-containing polymer gel film is coated with the animal cells which are adhered to the film.

Preferably, the water-containing polymer gel film contains chitosan.

Preferably, the water-containing polymer gel film has a dry film thickness of 5 µm to 200 µm, both inclusive.

Preferably, 2 to 10 types of animal cells are used as the animal cells.

Preferably, the animal cells are stacked in 2 to 10 layers.

The present invention further provides a method of culturing animal cells, which comprises supplying different liquids to one and the other sides of a water-containing polymer gel film having animal cells adhered onto at least one of the surfaces thereof by using the device according to the present invention.

The present invention further provides an animal cell culture obtained by the method according to the present invention.

The present invention further provides a device for culturing cells by supplying a culture solution to cells adhered onto a water-containing polymer gel film for adhering cells to be cultured, which comprises:

a first pressure equalizing mechanism for establishing a uniform dynamic pressure of a pipe section across a width of a culture device after the culture solution is introduced to the culture device through a pipe or pipe shaped structure;

a flow channel starting from the first pressure equalizing mechanism and having a uniform thickness of 1 mm or less, namely a uniformity of the order of µm in the thickness direction, for supplying the culture solution toward the flow direction;

a cell culture section provided midway through along the flow channel;

a flow channel provided downward the cell culture section and having a uniform thickness of 1 mm or less, namely a uniformity of the order of µm in the thickness direction; and an outlet pipe or pipe-shaped structure downward the downward flow channel.

Preferably, the first pressure equalizing mechanism is a pocket structure for establishing a uniform pressure of the liquid supplied to the culture device at the outlet.

Preferably, a second pressure equalizing mechanism for stabilizing the flow discharged from the culture device is further provided downstream of the downstream flow channel of the cell culture section.

Preferably, the second pressure equalizing mechanism is a pocket structure for establishing a uniform pressure of the liquid flowing from the culture device through the cell culture section into a pressure controlling mechanism.

Preferably, the pocket structure has a volume capable of storing at least twice the amount of the liquid flowing into the pocket structure per unit time, and the vectorial direction of an incoming flow does not directly overlap with that of a flow outgoing from the pocket.

Preferably, the cell culture section has a square configuration across the flow of the culture solution.

Preferably, a temperature control means for equalizing culturing conditions is provided at a flow channel section of the device.

Preferably, the device is constructed so as to be divided to at least a flow channel forming section, a cover section and a cell culture section.

Preferably, the device has a structure capable of supplying different liquids to one and the other sides of a water-containing polymer gel film.

Preferably, the device further comprises pressure detecting means for detecting pressure of a liquid flowing through a flow channel.

Preferably, the pressure detecting means is provided to a pipe upstream of the first pressure equalizing mechanism at the inlet side of the liquid.

Preferably, liquid feeding means is a continuous feed pump of a cylinder-switch type pressure driving system.

Preferably, the liquid feeding means is a microsyringe or microplunger pump.

Preferably, the device further comprises a pressure change absorbing mechanism for controlling the state of the liquid supplied to the cell culture section to be at predetermined conditions.

Preferably, the pressure change absorbing mechanism is a gas chamber, which is positioned upstream of the cell culture section of the device.

Preferably, a pressure control mechanism for controlling the pressure of the liquid to be supplied to the cell culture section to be at a predetermined value is provided in the gas chamber.

The present invention further provides a method of culturing cells wherein the cell culture device according to the present invention is used.

Preferably, the cells to be cultured are animal cells.

Preferably, the method comprises supplying a liquid while controlling the pressure of the liquid flowing through a flow channel to be at a predetermined value.

Preferably, the liquid is supplied while controlling the means for feeding the liquid by using a signal of the flow rate or the pressure of the liquid in the culture device.

The present invention further provides a device for culturing cells by supplying a culture solution to cells adhered onto a water-containing polymer gel film for adhering cells to be cultured, which comprises:

temperature controlling means provided near a flow channel at three or more sites including a site of a cell culture section and sites upstream and downstream thereof so as to independently control temperatures; and heat insulating means provided between adjacent temperature controlling means respectively such that the temperatures of temperature controlling means do not affect each other.

Preferably, the heat insulating means has a heat insulating structure using a vacuum.

Preferably, the heat insulating means has an air heat insulating structure which is formed by cutting a member forming a part of the culture device.

Preferably, the device further comprises temperature controlling means which enables to control temperature from outside a cover in addition to the flow channel forming layer side.

Preferably, the device has a structure capable of supplying different liquids to one and the other sides of the water-containing polymer gel film.

The present invention further provides a device for culturing cells by supplying a culture solution to cells adhered onto a water-containing polymer gel film for adhering cells to be cultured, which comprises:

liquid pressurizing means for pressurizing a liquid to be supplied to the cell culture device; and flow rate measuring means for measuring a flow rate of the liquid so as to supply the liquid to the culture device at a predetermined flow rate.

Preferably, a raw material supply tank is connected to the cell culture device, the liquid pressurizing means is connected to the raw material supply tank, and the flow rate measuring means is connected between the raw material supply tank and the cell culture device.

Preferably, a raw material preparation tank is connected to the raw material supply tank, the culture solution is supplied from the raw material preparation tank to the raw material supply tank, and then the culture solution is supplied from the raw material supply tank to the cell culture device.

Preferably, the liquid pressurizing means is a servo valve.

Preferably, the flow rate measuring means is a flowmeter.

Preferably, the flow rate measuring means is a pressure gauge.

Preferably, the device has a structure capable of supplying different liquids to one and the other sides of a water-containing polymer gel film.

Figure 1:
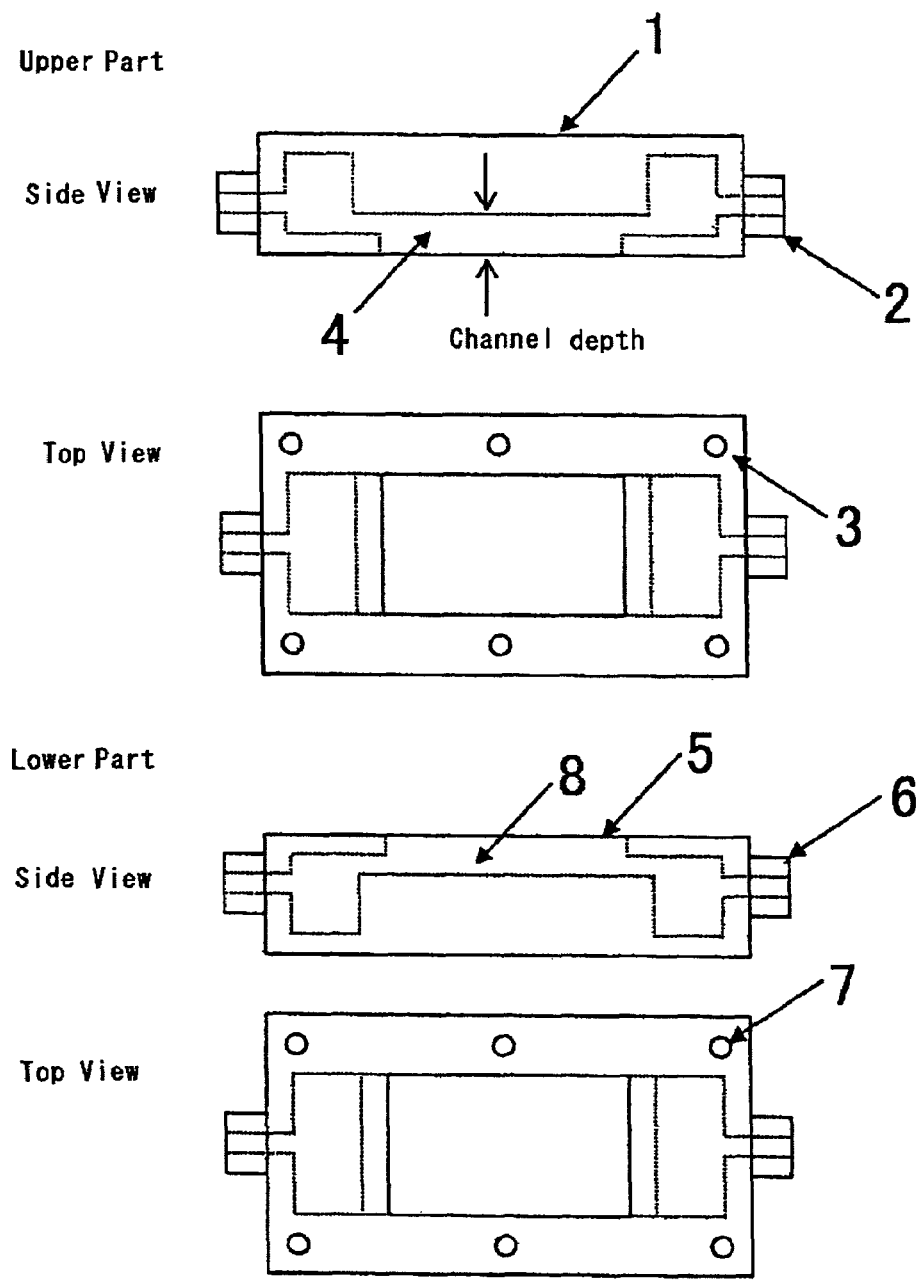
FIG. 1 shows a side view and a top view of each of the upper part and the lower part of one embodiment of the cell culture device according to the present invention.

In the figures, 1 denotes upper part, 2 denotes hose connecting portion, 3 denotes screw hole, 4 denotes flow channel, 5 denotes lower part, 6 denotes hose connecting portion, 7 denotes screw hole, 8 denotes flow channel, 9 denotes stainless steel member for holding water-containing polymer gel film, 10 denotes screw hole, 11 denotes pipe or pipe-shaped structure, 12 denotes first pressure equalizing mechanism, 13 denotes flow channel, 14 denotes cell culture section, 15 denotes downstream-side flow channel, 16 denotes outlet pipe or pipe-shaped structure, 17 denotes second pressure equalizing mechanism, 21 denotes pressure detecting means (pressure sensor), 22 denotes first pressure equalizing mechanism, 23 denotes liquid supply tank, 24 denotes culture unit, 25 denotes recovery tank, 31 denotes inlet-side pocket structure, 32 denotes gas chamber, 41 denotes temperature controlling means, 42 denotes temperature controlling means, 43 denotes temperature controlling means, 44 denotes heat insulating means, 51 denotes raw material preparation tank, 52 denotes raw material supply pump, 53 denotes raw material supply tank, 54 denotes pressurizing gas, 55 denotes pressurizing means, 56 denotes flowmeter, 57 denotes culture unit, and 58 denotes recovery tank.

THE PREFERRED EMBODIMENTS FOR CARRYING OUT THE INVENTION

Embodiments of the present invention will now be described in detail.

The cell culture device of the present invention is used for culturing cells attached to a water-containing polymer gel film by supplying a culture solution to the film.

The water-containing polymer gel film used in the present invention is used for attaching animal cells to at least one side of the surfaces thereof. Any polymer material can be used having a mesh structure formed by chemical bonds and holding a large amount of water in the meshes. Examples of polymer compounds which form hydrogel include anionic polysaccharides (for example, alginic acid, hyaluronic acid, chondroitin sulfate, dextran sulfate, agaropectin, carageenan, carboxymethyl cellulose), and salts thereof; cationic polysaccharides (for example, chitosan, partly-deacetylated chitin, aminated cellulose), and salts thereof; nonionic polysaccharides (for example, dextran, cellulose, cellulose acetate, hydroxyethylcellulose, methylcellulose, agarose, amylose, and glycomannan); polypeptides (for example, collagen, gelatin, and silk fibroin); synthetic polymers (for example, polyacrylic acid, polyacrylamide, poly-N-isopropylacrylamide, polyethylene imine, polyvinyl alcohol, and polyethylene glycol); inorganic substances (for example, silica gel); and mixtures and complexes of these.

As the water-containing polymer gel used in the present invention, a chitosan-containing gel is preferably used. Examples of the chitosan-containing gel used herein include a water insoluble chitosan which is obtained by dissolving chitosan in an acid to increase pH, and a polyionic complex formed of chitosan and a water-soluble anionic polymer (for example, alginic acid, hyaluronic acid, chondroitin sulfate, dextran sulfate, agaropectin, carageenan, carboxymethyl cellulose, polyacrylic acid or a copolymer thereof, polymethacrylic acid or a copolymer thereof, or polystyrene sulfonate or a copolymer thereof), or an amphoteric polymer (for example, gelatin or collagen). Examples of a method of preparing a polyionic complex include a method in which an aqueous chitosan solution is mixed with an aqueous anionic or amphoteric polymer solution, and a so-called layer-by-layer method in which a substrate is alternately soaked in an aqueous chitosan solution and an aqueous amphoteric polymer solution. When the layer-by-layer method is used, the uppermost layer (a final soaking solution) is preferably formed of chitosan. The chitosan containing gel used herein may contain a compound which is not directly involved in gelation.

The thickness of a water-containing polymer gel used herein preferably falls with in the range of 5 to 200 μm both inclusive by dry film thickness, most preferably, in the range of 10 to 100 μm both inclusive. If the thickness of a water-containing polymer gel is thin, the gel has poor strength and will be broken when a culture solution is flowed. In contrast, if the gel is too thick, it takes long time for a substance to be dispersed therein.

In the cell culture device of the present invention, at least one of the surfaces of a water-containing polymer gel is preferably coated with an animal cell adhesive material. The animal cell adhesive material that can be used in the present invention varies depending upon the type of cells to be cultured; however, a polypeptide is preferably used. As such a polypeptide, either naturally-occurring or synthetic peptide may be used as long as it is a so-called cell-adhesive peptide, non-cytotoxic and capable of adhering to animal cells in general culture conditions. Preferably, a layered extracellular matrix component gel is used. The extracellular matrix is defined as "a stable biological structure present outside a cell of an animal tissue, and a complicated assembly of biopolymers synthesized by the cell, secreted and accumulated outside the cell" (Biochemical Dictionary, Third edition, p. 570, published by Kagaku Dojin Kabushiki-kaisha). The extracellular matrix plays roles of materially supporting a cell and controlling the activity of the cell (in other words, a role of transmitting extracellular information to the cell, thereby changing its activity). The polypeptide as an extracellular matrix component means a constitutional component of an extracellular matrix. Specific examples thereof include collagen, elastin, proteoglycan, fibronectin, laminin, vitronectine, gelatin, and the like. Of them, collagen, atelocollagen, and Matrigel (a gel composed of type IV collagen, laminin and heparan sulfate) can be mentioned. An extracellular matrix component can be obtained in accordance with a routine method. Also, a commercially available extracellular matrix component may be used. The gelation of an extracelluar matrix component can be performed in accordance with a routine method. For example, when collagen is used as an extracellular matrix component, a collagen gel can be obtained by incubating 0.3 to 0.5% aqueous collagen solution at 37° C. for 10 to 20 minutes. A gelling agent may be used if necessary in the gelatinization of an extracellular matrix component.

In the cell culture device of the present invention, animal cells are cultured on at least one of the surfaces of a water-containing polymer gel film. Specific examples of animal cells that can be cultured include fibrocytes, vascular endothelial cells, cartilage cells, liver cells, small intestine epithelial cells, epidermis keratinized cells, osteoblasts, bone marrow mesenchymal cells, embryonic stem cells, and somatic stem cells. In the culturing of animal cells, generally a culture solution (e.g., D-MEM medium, MEM medium, HamF12 medium, or HamF10 medium) containing cells in a concentration of 10,000 to 15,000 cells/ml, is added onto a cell adhesive gel layer. The culture condition of animal cells may be appropriately selected depending upon the cells to be cultured. When cells are cultured on the cell adhesive gel layer, culturing is generally performed until a confluent single cell layer is formed on the cell adhesive gel layer.

Culturing of animal cells using a cell culture carrier (water-containing polymer gel film) can be performed as follows. A water-containing polymer gel film is placed in a plate such as a Petri dish. An appropriate culture solution (e.g., D-MEM medium, MEM medium, HamF12 medium, or HamF10 medium) is added, allowed to penetrate into the gel film for 5 minutes, and exchanged with a fresh medium. After this procedure is repeated three times, the Petri dish is allowed to stand alone for 12 to 24 hours, thereby impregnating the cell culture carrier (water-containing polymer gel film) with the culturing solution. After the culture solution in the Petri dish is discarded, cells are seeded on the cell adhesive gel layer of the cell culture carrier, and an appropriate culture solution (e.g., D-MEM medium, MEM medium, HamF12 medium, or HamF10 medium) is added to the Petri dish. The Petri dish is allowed to stand at 37° C. for 1 to 2 hours to adhere cells onto the cell adhesive gel layer, and thereafter culturing is continued at 37° C. During culturing, a culture solution may be exchanged as needed. The culture solution is generally exchanged at intervals of 0.5 to 2 days. Subsequently, the water-containing polymer gel is installed in a culture device, and a culture solution is supplied thereto by a pump.

As an alternative way, a water-containing polymer gel film is installed in a culture device in advance, and a liquid having cells dispersed therein is fed to the surface of the water-containing polymer gel film, and the cells are adhered, grown and cultured.

In the device of the present invention, the number of the types of animal cells that are cultured together is preferably 2 to 10 both inclusive. A plurality of animal cell types can be cultured by an in-plane co-culture process (a process for culturing different types of cells placed on a water-containing polymer gel film) or by stacked layer culture process. Specific example of the in-plane co-culture process, mention is made of a process of culturing cells such as fibrocytes and liver cells capable of adhering only to a polypeptide, followed by culturing cells such as vascular endothelial cells capable of adhering to an anionic polysaccharide.

The stacked layer culture process can be performed by stacking a cell sheet separately prepared, on the animal cell culture which is prepared by using a cell culture device of the present invention. This is also a preferable embodiment of the present invention. The number of layers is preferably 2 to 10 both inclusive. When vascular endothelial cells and liver cells are used as animal cell layers to be stacked, a three-dimensional liver tissue construct can be formed. This three-dimensional tissue construct can be applied to a drug permeability test in vitro, and applied to an experimental model in place of an animal and used as an organ for transplantation. The stacked animal cell layer can be cultured in culture conditions depending on the type of cells which constitute the cell layer. As a medium used in culturing, for example, D-MEM medium, MEM medium, HamF12 medium, or HamF10 medium may be mentioned. When a cell culture using a water-containing polymer gel film is an in-plane co-culture, a three-dimensional cell tissue can be constructed by stacking the cell culture layers.

The cell culture device of the present invention may have a structure in which different liquids can be supplied to one and the other sides of a water-containing polymer gel film. By virtue of such a device, animal cells can be cultured while supplying different liquids to one and the other sides of the film respectively. The term "different liquids" used herein include a case where the same types of liquids are separately supplied without circulation; however, it is preferred that the liquid supplied to one side differs in composition from that supplied to the other side. As a liquid which is supplied to animal cells, a liquid analogous to blood, for example, a liquid containing D-MEM medium, MEM medium, HamF12 medium, or HamF10 medium saturated with oxygen, may be mentioned. As a liquid to be supplied to the opposite side to the animal cells, a liquid analogous to bile, for example, D-MEM medium, MEM medium, HamF12 medium, HamF10 medium, or isotonic phosphate buffer may be mentioned. Bile acid may be added to the liquid as a bile component. The flow rate of a liquid is preferably controlled so as to apply a flow shearing force of 2.0 dyn/cm$^2$ or more to cells, most preferably 2.0 to 3.0 dyn/cm$^2$. To apply flow shearing force to cells, a microreactor is preferably used as the culture device of the present invention. The size of the culture device of the present invention is not particularly limited as long as an appropriate shearing force can be applied to cells, and may range from the order of meters (for producing a substance) to micro meters (as a sensor), depending on the purpose.

In the cell culture device of the present invention, a flow channel can be formed by the water-containing polymer gel film and the inner wall of the culture device. In this case, the space between the water-containing polymer film and the inner wall of the culture device is preferably within the range of 10 μm to 2 mm, both inclusive, most preferably, 20 μm to 1 mm, both inclusive. If the space is too narrow, animal cells may be in contact with the inner wall of the culture device. As a result, a liquid cannot flow. In contrast, if the space is extremely large, the supply of a substance to animal cells from the liquid flow, especially from a distant part of the liquid flow, is delayed and it becomes difficult to apply appropriate shearing to animal cells.

The flow channel mentioned above can be constructed on a solid substrate by a microfabrication technique. Examples of a material to be used include a metal, silicon, Teflon (registered trademark), glass, ceramic and plastic. When heat resistance, pressure resistance and solvent resistance are required, metal, silicon, Teflon (registered trademark), glass or ceramic may be preferably used, most preferably, a metal is used. Examples of such a metal include nickel, aluminium, silver, gold, platinum, tantalum, stainless steel, hastelloy (Ni—Fe based alloy) and titanium. Preferably, highly corrosion-resistant stainless steel, hastelloy and titanium are used.

When an acidic substance is handled in a conventional batch-type reaction device, a unit of metal (stainless steel, etc.) having a surface which is coated with glass, is used. Such a glass-coated metal may be used for the microreactor. The coating material is not limited to glass. Another metal or other material may be applied on a metal as a coating material, depending on the purpose. Alternatively, a non-metal material (e.g., ceramic) may be coated with a metal or glass.

Representative examples for microfabrication techniques for forming a flow channel include LIGA technique using X-ray lithography, high aspect-ratio photolithography using EPON SU-8, micro electrical discharge machining, (μ-EDM), high aspect-ratio processing of silicon using Deep RIE, Hot Emboss processing, optical construct method, laser processing, ion beam processing, and mechanical micro cut processing using a micro-tool made of a hard material such as diamond. These techniques may be used alone or in combination. Preferable microfabrication techniques include LIGA using X-ray lithography, high aspect-ratio photolithography using EPON SU-8, micro electrical discharge machining (μ-EDM), and mechanical micro cut processing.

To assemble the cell culture device (bioreactor) of the present invention, a bonding technology can be used. General bonding technologies are roughly classified into solid-phase bonding and liquid-phase bonding. Examples of typical bonding methods generally used include pressure welding and diffusion bonding, as a solid bonding; and, welding, eutectic bonding, soldering, and adhesion as a liquid-phase bonding. Furthermore, in assembling, it is desirable to use a highly accurate bonding method capable of maintaining dimensional accuracy and free from degradation of a material with high-temperature heating and destruction of a microstructure such as a flow channel, caused by significant distortion. Examples of such a bonding technology include silicon direct bonding, anodic bonding, surface activation bonding, direct bonding using a hydrogen bond, bonding using an aqueous HF solution, Au—Si eutectic bonding, and void-free bonding.

In the cell culture device of the present invention, animal cells are cultured while flowing through a flow channel. Depending upon a purpose, surface treatment may be applied to the flow channel of the cell culture device of the present invention. The surface treatment is important, because adsorption of a sample to glass or silicon sometimes causes a problem, particularly in the case of using an aqueous solution. When a fluid control is performed in a micro-scale flow channel, it is desirably performed without installing therein a movable part requiring a complicated manufacturing process. For example, if surface treatment is applied to form a hydrophilic region and a hydrophobic region within a flow channel, it becomes possible to operate a fluid by using the difference in surface tension working in the boundary of the regions.

In order to introduce and mix a reagent and a sample in the micro-scale flow channel of the cell culture device, a fluid controlling function is required. In particular, the behavior of a fluid in a micro-space area differs from that in a macro-space area. Therefore, a control system suitable for the micro-scale area must be devised. When fluid controlling systems are classified based on the operational style, they are divided into a continuous flow system and a liquid drop (liquid plug) system. When they are classified based on driving force, they are divided into an electrical driving system and a pressure driving system. These systems will be described in detail below.

The most widely used system for controlling a fluid is a continuous flow system. In the fluid control by the continuous flow system, the entire flow channel of a culture device is filled with a fluid, and the entire fluid is generally driven by a pressurizing source such as a syringe pump provided outside the system. This system has an advantage in that a control system can be relatively simply set up; however, it has the following disadvantages. First, it is difficult to deal with the case having a plurality of reaction steps and exchange of samples involved therein. Second, a system is arranged but a low degree of freedom. Third, since a solution itself is a medium to be driven, a dead volume is large. As a different system from the continuous flow system, a liquid-drop system (liquid plug) is known. In this system, liquid drops partitioned by air are moved in a culture unit and a flow channel communicating with the culture unit. Individual liquid drops are driven by air pressure. The culture device system must have, within the system, a vent structure for releasing air between liquid drops and the flow-channel wall or between liquid drops, to the outside as needed, and a valve structure for maintaining pressure within a branched flow channel independently of other portion. In addition, in order to regulate liquid drops by controlling pressure difference, it is necessary to construct a pressure control system composed of a pressurizing source and a switch valve, outside the system. As described above, in the liquid drop system, the constitution of the device and the structure of the culture unit are slightly complicated; however, a multiple-stage operation can be performed, which allows several reactions to sequentially perform by operating a plurality of liquid drops individually. Therefore, the degree of freedom in arranging the system increases.

As a driving system for controlling a fluid, generally, an electrical driving method and a pressure driving method are widely used. In the electrical driving method, high electric voltage is applied to both ends of a flow channel to generate an electric seepage flow, thereby moving a fluid. On the other hand, in the pressure driving method, pressure is applied to a fluid by a pressurizing source provided outside, thereby moving the fluid. Both methods differ in behavior of a fluid as described below: In the electrical driving system, a flow rate profile seen in the sectional view of a flow channel is flat (flat distribution), whereas, in the pressure driving system, hyperbolic (fast at the center of the flow channel, but slow at edge areas near the wall). From this, the electrical driving method is suitable in the case where a sample is desired to move while keeping the shape such as a sample plug. In the case of the electrical driving system, a flow channel must be filled with a fluid, so that a continuous flow system is inevitably employed. However, since the operation of a fluid can be electrically controlled, a relatively complicated operation can be realized such as a time-dependent concentration gradient obtained by mixing two types of solutions while changing the mixing ratio thereof. On the other hand, the pressure driving system can control any liquid no matter what electrical characteristics the liquid has. In addition, since any side effects such as heat generation and electrolysis may not be considered, a substrate is substantially free from damages. Therefore, the pressure driving system is applied in a wide range. On the contrary, a pressurizing source must be provided outside the system, and the response characteristics of an operation vary depending upon whether the dead volume of the pressure system is larger or small. Therefore, these complicated operations must be automated.

A method for controlling a fluid can be appropriately selected according to its purpose; however, preferably a continuous flow system using a pressure driving system is used.

The temperature control of a cell culture device can be performed by placing the entire culture device in a container in which temperature is controlled or by employing a thermal cycle. More specifically, a heater construct, such as a metal resistance wire or polysilicon, is arranged in the device for warming, and natural cooling is used for cooling. Temperature is sensed as follows. In the case where a metal resistance wire is used, another resistance wire is installed. Temperature is detected by measuring a change in resistance value of the another resistance wire. In the case where polysilicon is used, temperature is detected by use of a thermo couple. Alternatively, heating and cooling may be performed from the outside of the system by bringing a peltiert element into contact with a culture device. Which method is used may be determined based on the use and the material of the main body of the culture device.

The cell culture device of the present invention can be sterilized in any method. As a sterilization method, alcohol sterilization, wet pasteurization, dry heat sterilization, EOG sterilization, and radiation sterilization using an electron beam, γ ray, X-ray and UV ray are preferably used. Of them, preferably radiation sterilization, more preferably, electron-beam sterilization may be used. The irradiation dose in the electron beam sterilization preferably falls within 0.1 kGy to 65 kGy, both inclusive and most preferably 1 kGy to 40 kGy, both inclusive. Chemical sterilization such as EOG sterilization, and high-hear sterilization such as high-pressure vapor gas sterilization are not preferable since a cell adhesion layer and an alginic acid gel layer are decomposed. The cell culture carrier (water-containing polymer gel film) thus sterilized can be stored for a long time at room temperature as long as it is placed in aseptic conditions. The aforementioned sterilization methods may be used alone or in combination of a plurality of methods, or otherwise, a single sterilization method may be used repeatedly.

Figure 2:
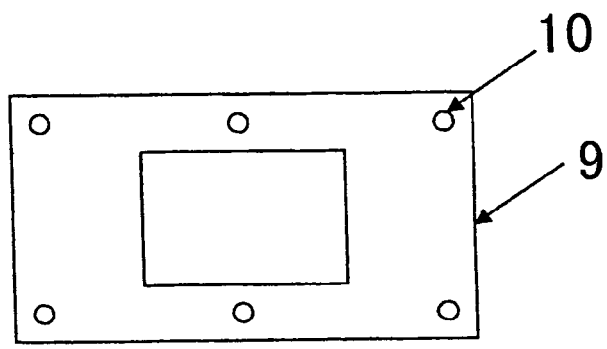
FIG. 2 shows a stainless steel member for holding a water-containing polymer gel film of one embodiment of the cell culture device according to the present invention.
Figure 3:
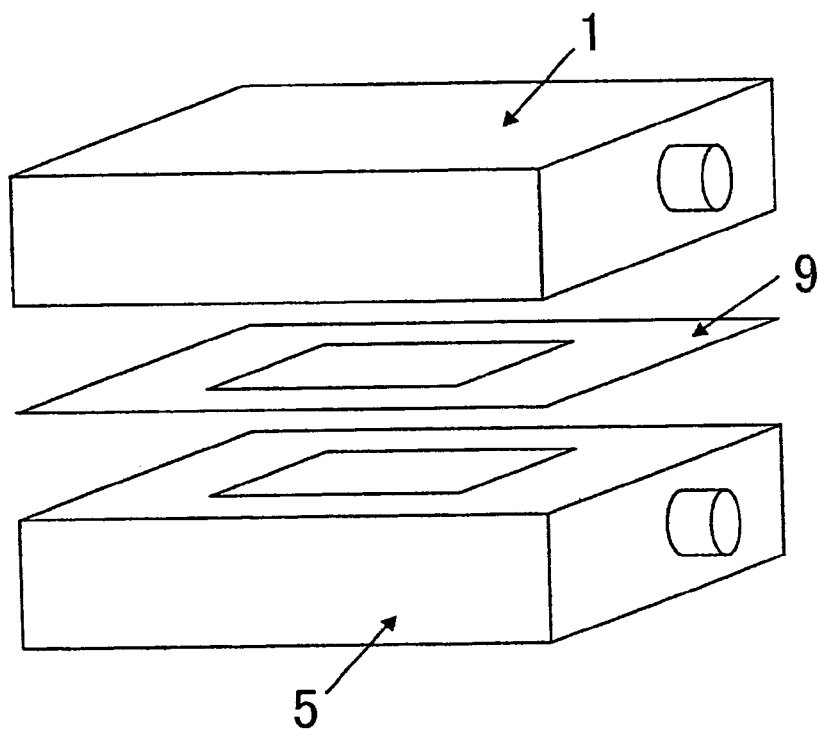
FIG. 3 shows the structure of one embodiment of the cell culture device according to the present invention.

One example of the structure of the cell culture device of the present invention is shown in FIGS. 1 to 3. The bioreactor shown in FIGS. 1 to 3 comprises a stainless steel part 9 for holding a water-containing polymer gel film (shown in FIG. 2) sandwiched between an upper part 1 and a lower part 5 (shown in FIG. 1) as shown in FIG. 3. In the upper and lower parts 1 and 5, flow channels 4 and 8 are formed, respectively. To both ends of the flow channels 4 and 8, hose connecting portions 2 and 6 are formed, respectively. To the upper part 1, lower part 5, and stainless steel part 9 for holding a water-containing polymer gel film, screw holes 3, 7 and 10 are formed respectively at positions corresponding to each other. Individual parts can be integrated by putting screws in screw holes and tightening them.

The characteristics of the cell culture device of the present invention will now be described with reference to FIGS. 4 to 6.

Figure 4:
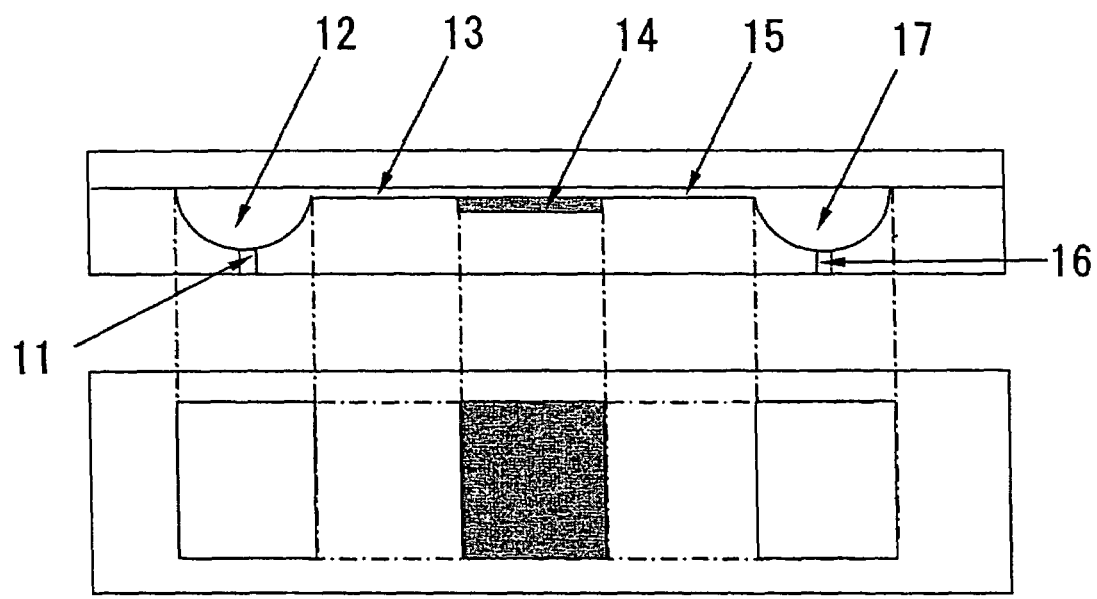
FIG. 4 shows the structure of one embodiment of the cell culture device according to the present invention having a pressure equalizing mechanism (pocket structure)

The cell culture device of the present invention shown in FIG. 4 is characterized by comprising a first pressure equalizing mechanism 12 for equalizing the dynamical pressure of a culture solution of a pipe portion along the width direction of the cell culture device after the culture solution is supplied through a pipe or a pipe-shaped structure 11. In the cell culture device of the present invention shown in FIG. 4, a flow channel 13, through which a culture solution flows forward, has a uniform thickness of 1 mm or less, namely uniformity of the order of μm. A cell culture section 14 is provided midway through the flow channel. Downstream of the cell culture section 14, a downstream flow channel 15 having a uniform thickness of 1 mm or less with uniformity of the order of μm is provided. Further downstream of the downstream flow channel portion 15, an outlet pipe or pipe-shaped structure 16 is arranged. In the cell culture device of the present invention shown in FIG. 4, a second pressure equalizing mechanism 17 for stabilizing the flow sent from the culture device is arranged downstream of the downstream flow channel 15 of the cell culture section. In the cell culture device of the present invention shown in FIG. 4, the first pressure equalizing mechanism 12 is a pocket structure for equalizing the pressure of a liquid to be supplied to a culture section at its outlet, whereas the second pressure equalizing mechanism 17 is a pocket structure for equalizing the pressure of the liquid which flows out of the culture section 14 into a pressure controlling mechanism. It is preferable that the pocket structure mentioned above can keep at least twice as large as volume of a liquid supplied to the pocket structure per unit time. It is also preferable that the vector of an incoming flow does not directly overlap with that of an outgoing flow from the pocket structure. Furthermore, it is preferable that the cell culture section 14 has a square configuration across the culture solution flow. A temperature controlling means for providing uniform culture conditions may be provided in the flow channel of the cell culture device. The cell culture device of the present invention is preferably constructed such that it can be decomposed into at least flow channel forming section, cover portion and cell culture section. Furthermore, it is preferable that an orifice part which is thinner than the flow channel 13 may be provided between the pocket structure portion and the flow channel 13.

Figure 5:
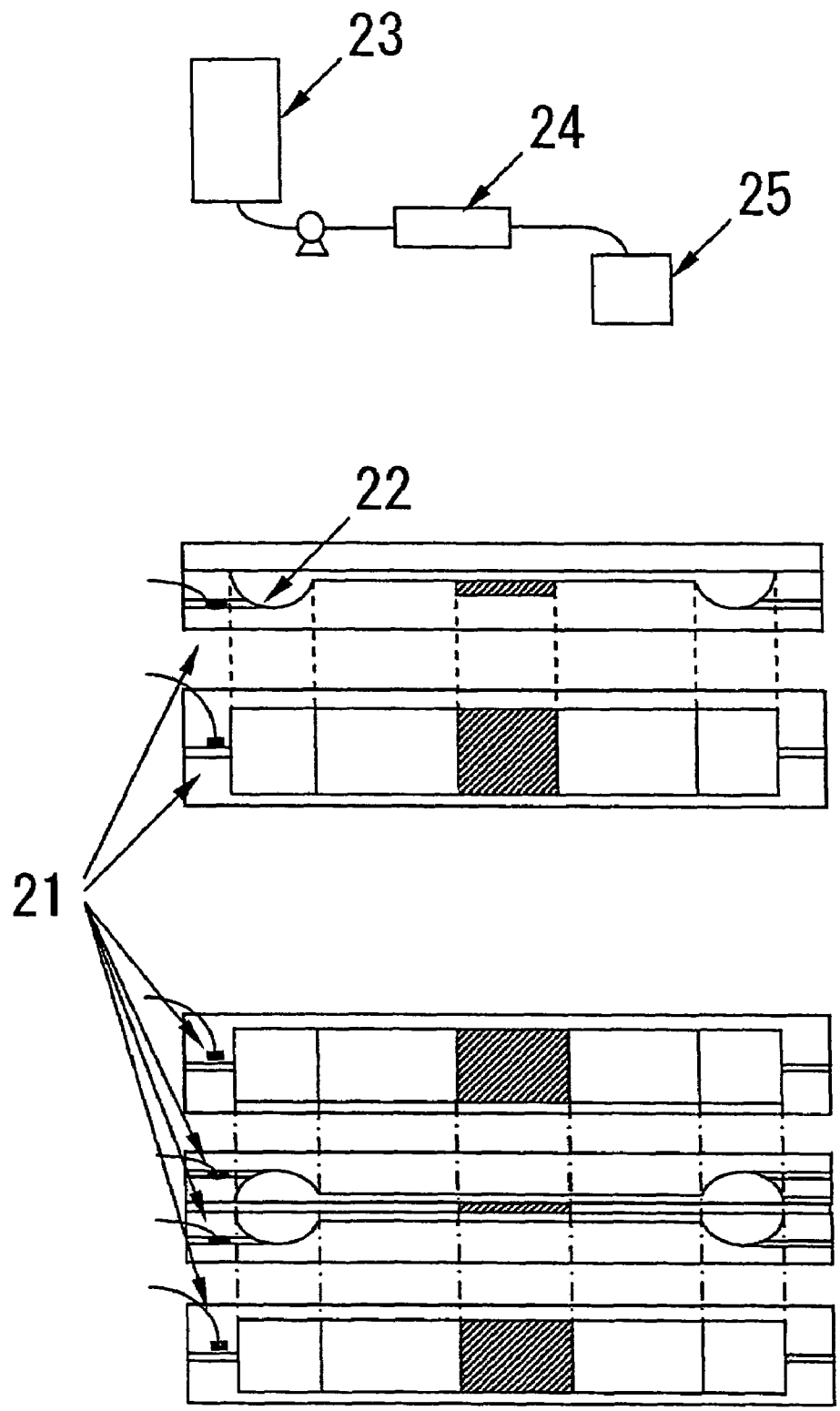
FIG. 5 shows the structure of one embodiment of the cell culture device according to the present invention having pressure detecting means (pressure sensor)

In the cell culture device of the present invention shown in FIG. 5, a pressure detecting means (pressure sensor) 21 for detecting the pressure of a liquid flowing through a flow channel is further provided. Preferably, the pressure detecting means 21 is provided to a pipe ahead of the first pressure equalizing mechanism 22 at the liquid inlet side. In the upper stage of FIG. 5, one example of a structure of a system including the cell culture device of the present invention is shown. A culture solution is supplied from a liquid supply tank 23 to a culture device 24 and then discharged to a recovery tank 25.

A method for controlling a flow can be appropriately chosen depending upon the purpose. A continuous flow system using a pressure driving system is preferably used. Representative examples of a liquid-feed method include an alternate driven type microsyringe, microgear pump, and multi-head microplunger pump. This method enables an operation continuously for a long time in a relatively simple control manner; however, a flow rate changes during a steady operation time, and pulsation generates when a heads is exchanged. Therefore, a liquid-feed method must be appropriately chosen depending upon the purpose.

The temperature control of a cell culture device can be performed by placing the entire culture device in a container whose temperature is controlled or by employing a thermal cycle. More specifically, a heater construct, such as a metal resistance wire or polysilicon is arranged in the device for warming, and natural cooling is used for cooling. Temperature is sensed as follows. In the case where a metal resistance wire is used, another resistance wire is installed. Temperature is detected by measuring a change in resistance value of the another resistance wire. In the case where polysilicon is used, temperature is detected by use of a thermo couple. Alternatively, heating and cooling may be performed from the outside of the system by bringing a peltiert element into contact with the reactor. Which method is used may be determined based on the use and the material of the main body of the culture device. Any pressure detecting system may be used as long as it can detect minor pressure change and preferably may not interfere with a flow. As a pressure detecting system suitable for attaching to a micro structure, MEMS element-type, piezo-element type, and a ceramic element type are preferable.

Figure 6:
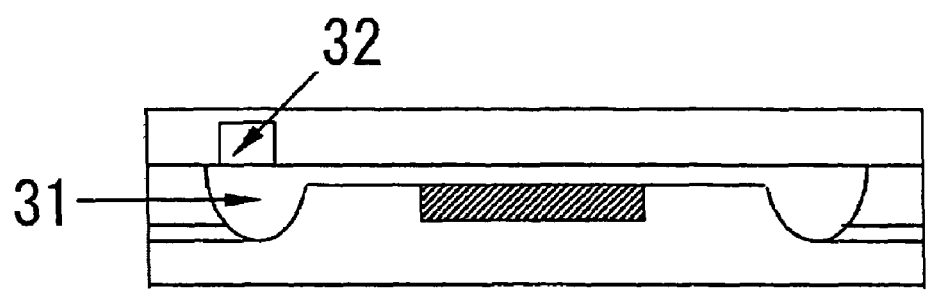
FIG. 6 shows the structure of one embodiment of the cell culture device according to the present invention having a pressure change-absorbing unit (gas chamber)
Figure 6:
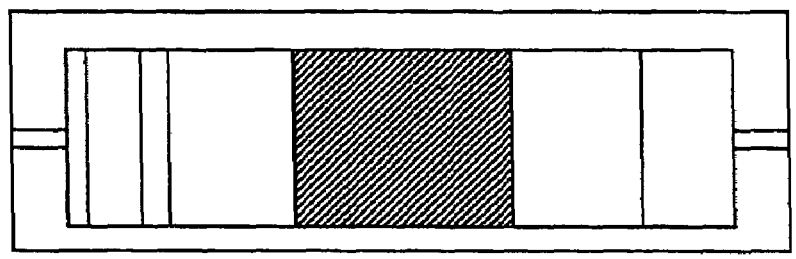
Figure 6:
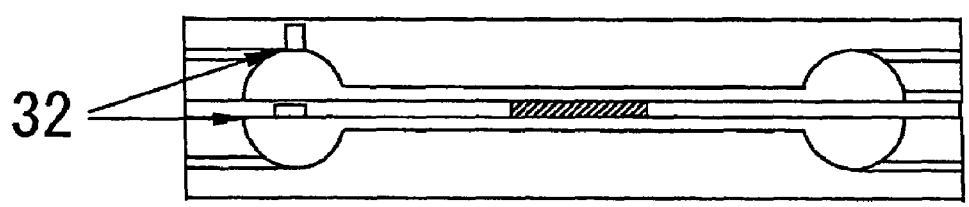
Figure 6:
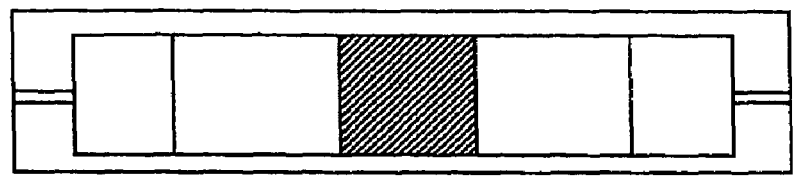

In the cell culture device of the present invention shown in FIG. 6, a gas chamber 32 is provided above an inlet-side pocket structure 31 of the culture device. Even if pulsation is generated by a liquid feed means, it can be absorbed by the gas chamber 32. Furthermore, the inner pressure of the gas chamber can be externally controlled so as to always keep a constant pressure.

The features of the cell culture device of the present invention will now be described with reference to FIG. 7.

Figure 7:
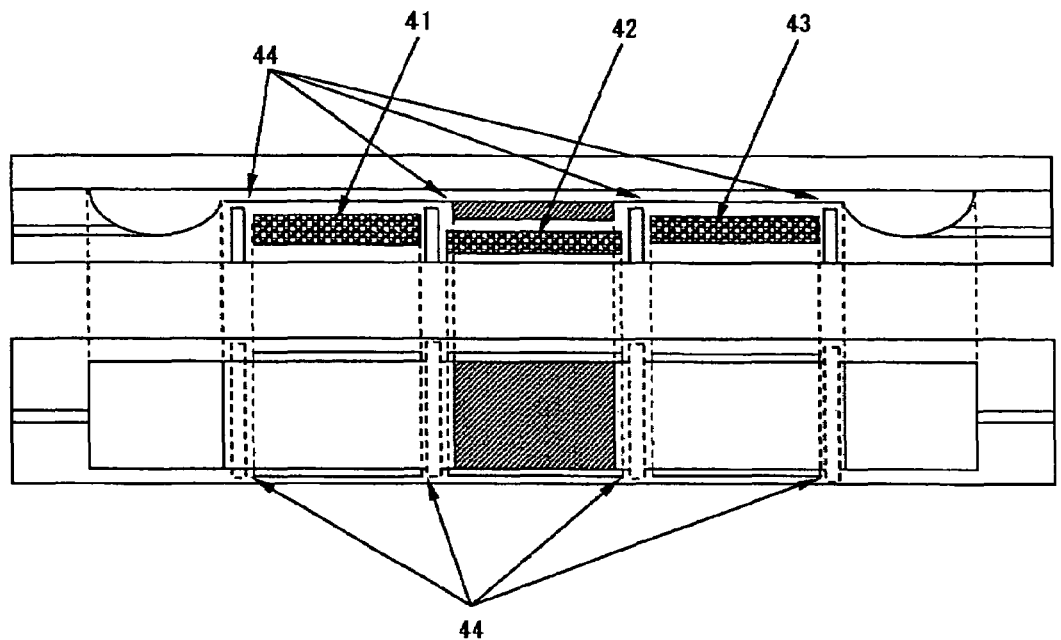
FIG. 7 shows the structure of one embodiment of the cell culture device according to the present invention having temperature controlling means and heat insulating means.

In the cell culture device of the present invention shown in FIG. 7, temperature controlling means 41, 42 and 43 for independently controlling temperature are provided near a flow channel at three or more sites, namely a site upstream of a cell culture section; a site of the cell culture section, and a site downstream portion of the cell culture section. The temperature controlling means 41 is responsible for controlling the temperature of a portion upstream of the cell culture section, the temperature controlling means 42 for the cell culture section, and the temperature controlling means 43 for a portion downstream of the cell culture section. Heat insulating means 44 are provided between adjacent temperature controlling means such that the temperatures of the adjacent temperature controlling means do not affect each other. According to the cell culture device of the present invention, there is provided a specific device for controlling the temperature of a culture section and the temperature of the liquid to be supplied to the culture section into a predetermined condition. Therefore, cells can be cultured under optimal temperature control by using the cell culture device of the present invention.

As a means for controlling temperature used in the present invention, a thermal cycle may be used. More specifically, a heater construct, such as a metal resistance wire or polysilicon is arranged in the device for warming, and natural cooling is used for cooling. Temperature is sensed as follows. In the case where a metal resistance wire is used, another resistance wire is installed. Temperature is detected by measuring a change in resistance value of the another resistance wire. In the case where polysilicon is used, temperature is detected by use of a thermo couple. Alternatively, heating and cooling may be performed from the outside of the system by bringing a peltiert element into contact with a culture device. Which method is used may be determined based on the use and the material of the main body of the culture device.

As the heat insulating means used in the present invention, a heat-insulting slit (vacuum heat insulating slit) may be mentioned. A heat-insulating material may be used to form the heat insulating slit. The type of heat insulating material can be selected depending upon use of the slit and the material of the main body of the culture device.

In the cell culture device of the present invention, cells can be cultured while controlling the flow rate of a liquid by a liquid pressurizing means for pressurizing the liquid to be supplied to a culture device and a flow rate measuring means for measuring the flow rate of the liquid so as to supply the liquid at a predetermined flow rate to the culture device.

As a driving system for controlling a fluid, an electrical driving method, in which high electric voltage is applied to both ends of a flow channel to generate an electric seepage flow, thereby moving a fluid, and a pressure driving method, in which pressure is applied to a fluid by a pressure source provided outside, thereby moving the fluid (including a method of pressurizing a liquid to transport the liquid and a method of providing a driving pressure to a liquid by a pump or the like), are generally and widely employed. Both methods have the differences in the behavior of a fluid as described below: In the electrical driving system, a flow rate profile seen in the sectional view of a flow channel is flat (flat distribution), whereas, in the pressure driving system, hyperbolic (fast at the center of the flow channel, but slow at edge areas near the wall). From this, the electrical driving method is suitable in the case where a sample is desired to move while keeping the shape such as a sample plug. In the case of employing the electrical driving system, since a flow channel must be filled with a fluid, a continuous flow system is inevitably employed. However, since the operation of a fluid can be electrically controlled, a relatively complicated operation is realized such as a time-dependent concentration gradient obtained by mixing two types of solutions while changing the mixing ratio thereof. Nevertheless, when cells are cultured in practice, a long time operation must be performed not for hours but days. Thus, the electrical driving system has a problem in the aspect of a long-time operation. Actually, when the device is operated for a long time, air bubbles generate and have an influence on a flow. Therefore, the electrical driving system has a problem in reliability.

On the other hand, a pump system, which is included in a pressure driving system if roughly classified, is advantageous since it is favorable in consideration of the size of experimental equipment and convenience and readily available because of a commonly used product. However, in this system, since a liquid is supplied by mechanical driving force, there are fears that abrasion may cause deterioration and leakage of the liquid. On the other hand, in a liquid-feed system for feeding a liquid by pressurizing it, which is a representative example of a pressure driving system, can control any liquid no matter what electrical characteristics the liquid has, compared to the electrical driving system. In addition, since any side effects such as heat generation and electrolysis may not be considered, a substrate is substantially free from damages. Therefore, the pressure driving system may be applied in a wide range. On the contrary, a pressurizing source must be prepared outside the system and the response characteristics to an operation vary depending upon whether the dead volume of the pressure system is larger or small. In addition, it is difficult to add a liquid in a continuous culture. To deal with the problems, complicated care and process are required.

The present invention realizes a device which utilizes a merit of the pressuring system and provides rapid response of an outside pressure device to overcome its inherent drawback, while allowing for continuous operation for a long period on the order of days by subsequently supplying a fresh culture solution according to the effective life of the culture solution.

Figure 8:
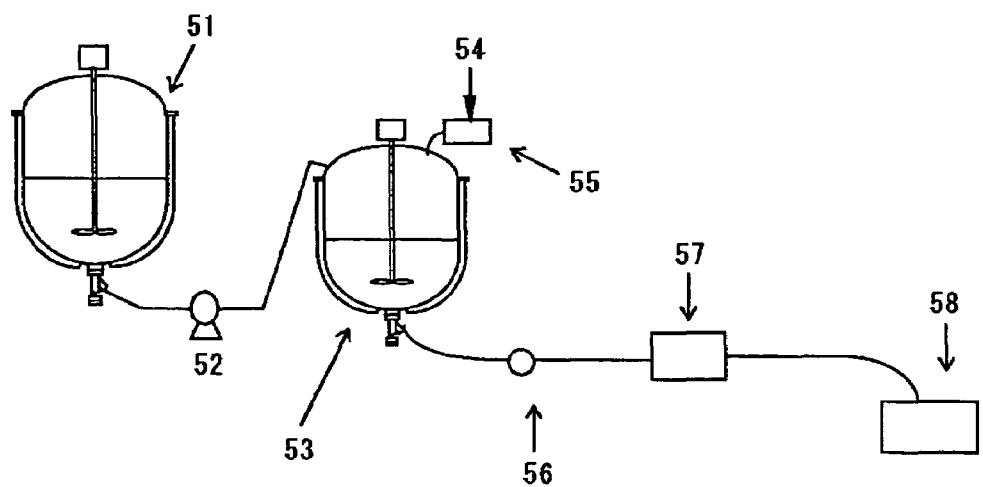
FIG. 8 shows the structure of one embodiment of the cell culture device according to the present invention having liquid pressurizing means and flow rate measuring means.

Next, characteristics of the cell culture device of the present invention will be described with reference to FIG. 8.

A raw material supply tank 53 for supplying a culture solution suitable for a test purpose to a culture device 57 is provided. This tank is equipped with a pressurizing means 55 (pressure controlling valve, etc.) for pressurizing the inner atmosphere of the tank to push the solution outside. Cells are cultured by supplying a pressurizing gas (air or an inert gas) 54 to the pressurizing means 55, while controlling the pressurizing means 55 such that a flow rate measured by a flow meter 56 (arranged between the culture unit 57 and the raw material tank 53) is set at a predetermined flow rate. In this system, a raw material preparation tank 51 is provided upstream of the raw material supply tank. The raw material preparation tank 51 supplies a liquid at appropriate intervals such that the effective life of the liquid in the raw material supply tank 53 may not expire and the liquid may not run out. The liquid of the tank 53 is pressurized by use of a servo valve, which immediately responds within milliseconds and changes the pressure of the tank in the order of 10 KPa. To attain an object for continuous cell culture operation, a liquid is supplied to the raw material supply tank by using a raw material supply pump 52. A raw material is supplied from a raw material preparation tank 51 to the raw material supply tank 53 by a pump capable of applying a higher pressure than that applied to the tank during the steady state where the liquid is continuously supplied to the culture unit with no liquid supplied from the upstream. As a natural consequence, the inner pressure of the raw material supply tank changes; however, the liquid can be fed stably by automatically controlling the applied pressure so as to maintain a predetermined flow rate as measured by a flow meter. The liquid flowing through the culture unit 57 is recovered to a recovery tank 58.

The present invention will be described in more detail by way of the following examples, but the present invention is not limited to these examples.

EXAMPLES

Example A-1

(1) Manufacture of Reactor

A bioreactor shown in FIG. 1 was manufactured by processing polymethyl methacrylate board by a mechanical micro-cut processing and polishing the cut surface. The depth of the flow channel formed in the upper part was set at 500 μm, whereas that formed in the lower part was set at 2 mm. Stainless steel of 100 μm thickness was processed as shown in FIG. 2 to prepare a part for holding a water-containing polymer gel film. This stainless steel part was installed in the bioreactor of FIG. 1 to obtain a construct shown in FIG. 3. Note that the figures are schematically drawn, so that dimensions and dimensional proportions are not consistent with those of the actual bioreactor.

(2) Manufacture of Water-containing Polymer Gel Film

First, 20 g of chitosan (CT-100, manufactured by Wako Pure Chemical Industries, Ltd.) was gradually added to 1000 g of an aqueous acetic acid solution (1% by mass). The solution mixture was stirred at 40° C. for 3 hours to dissolve chitosan and filtrated through microfilter FG-30 manufactured by Fuji Photo Film Co. Ltd. The filtrated aqueous acetic acid solution of chitosan was coated by an applicator onto a polyethylene terephthalate film (200 micron in thickness) prepared in advance to obtain a wet film of 250 micron thickness. The wet film was dried at 40° C. for 3 hours. The dried chitosan gel film was soaked in a methanol solution of sodium hydroxide (10% by mass) for 60 minutes and subsequently in a PBS solution for 60 minutes. Thereafter, the film was washed with running water for 60 minutes, dried at 40° C. for 3 hours to obtain a chitosan gel film. The thus obtained chitosan gel film was sterilized by UV rays for 3 hours to obtain a water-containing polymer gel film.

(3) Culturing of Animal Cells (i) Release-type Cell Culture Film

The chitosan gel film obtained in (2) above was soaked in a 0.1 mol/l aqueous solution of calcium chloride for 5 minutes. Thereafter, the chitosan gel film was taken out and placed on an SUS board so as not to make wrinkles. After water on the chitosan gel was absorbed by a sponge roller which was dried in advance at 40° C. for 1 hour, coating was performed by an applicator to obtain a wet film having a thickness of 500 micron. The coated product was soaked in an aqueous solution mixture of a 0.5 mol/l aqueous calcium chloride solution and a 0.05 mol/l aqueous solution of 1-ethyl-3-(3-dimethylaminopropylamino)carbodiimido hydrochloride for 60 minutes, subsequently washed with running water for 30 minutes, and transferred onto a Teflon plate. Thereafter, 15 g of an aqueous solution of CELLMATRIX type I-C (manufactured by Nitta gelatin) collagen (0.03% by mass) diluted with a 0.04 mol/l HEPES aqueous solution was casted and dried at 37° C. for a day and night. The film was sterilized by UV rays for 3 hours to obtain a release-type cell culture film.

(ii) Preparation of Stacked Cell Culture (a) Culture on Water-containing Polymer Gel Film
Cells used: HepG2 (cells derived from human liver cancer)
Medium used: Eagle's minimum essential medium (MEM), 10% fetal bovine serum
Cell culture carrier The water-containing polymer gel film of (2) above was placed in a Petri dish. A medium was added to the Petri dish, allowed to penetrate for 5 minutes, and exchanged with a fresh medium. After this procedure was repeated three times, the Petri dish was allowed to stand overnight, thereby penetrating the medium into cell culture carrier. Cells cultured in advance were recovered with trypsin treatment, and the cell concentration was adjusted to 50,000 cells/ml. After the cells and medium in the Petri dish were discarded, the cell solution was seeded into the Petri dish so as to obtain a cell concentration of 10,000 cells/cm$^2$, and then a medium was added. Thereafter, the Petri dish was subjected to incubation in a $CO_2$ incubator at 37° C. for 2 days.

(b) Culture on Release-type Cell Culture Film
Cells used: BAE (bovine aorta endothelial cells)
Medium used: Eagle' minimum essential medium (MEM), 10% fetal bovine serum
Cell culture carrier:

The release-type cell culture film of (3) (i) above was placed in a Petri dish. A medium was added to the Petri dish, allowed to penetrate for 5 minutes, and exchanged with a fresh medium. After this process was repeated three times, the Petri dish was allowed to stand overnight, thereby penetrating the medium into cell culture carrier. Cells cultured in advance were recovered with trypsin treatment, and the cell concentration was adjusted to 50,000 cells/ml. After the cells and medium in the Petri dish was discarded, the cell solution was seeded into the Petri dish so as to obtain a cell concentration of 10,000 cells/cm$^2$, and then a medium was added. Thereafter, the Petri dish was subjected to incubation in a $CO_2$ incubator at 37° C. for 2 days.

(c) Stacking of Cell Layers

On the cell culture prepared in the step (a), the cell culture prepared in the step (b) was stacked such that the cells of both cultures were in contact with each other and incubated in MEM medium overnight. The resultant cell culture was soaked in a release solution (MEM medium containing 3 mM 1-hydroxyethane-1,1-diphosphonic acid(HEDP)) for 10 minutes to dissolve a calcium alginate layer, thereby removing a nylon micro filter.

(4) Assembly of Reactor and Culturing

The cell culture of (3) above was installed in the frame of the stainless steel part 9 for holding a water-containing polymer gel film in the reactor of (1) above (shown in FIGS. 1 to 3). Further, MEM (as a medium A) was supplied to the cell layer side, and a solution containing cholic acid dissolved in an isotonic phosphate buffer (pH 7.2) at a concentration of 40 g/l (as medium B) was supplied to the opposite side of the cell layer. To simulate shearing by blood, culturing was performed by increasing the flow rate of medium A so as to apply, to the cells, a flow shearing force of 2.5 dyn/cm$^2$, which corresponds to the flow shearing force at a tissue wall. As a result, good cultured cells similar to those obtained in a living body were obtained. The release of less than 1% of the cell layer was observed in the cell culture of this Example.

Comparative Example A-1

The cell culture of (3) of Example A-1 was installed in the frame of the stainless steel part 9 for holding water-containing polymer gel film of the reactor of (1) of Example A-1 (shown in FIGS. 1 to 3). MEM medium was supplied to the opposite side of the cell layer and circulated by bonding upper and lower hose connectors. The flow rate was controlled so as to apply a flow shearing force of 2.5 dyn/cm$^2$ corresponding to that applied to a tissue wall. As a result, the release of 10% of the entire cells from the film was observed. The released cells had been dead.

Example A-2

The cell culture of (3) of Example A-1 was experimented in the same reactor as in (3) of Example A-1 except that the space between the inner wall of the reactor and the water-containing polymer gel film (the depth of the channel of the upper part) was set at 3 mm. As a result, a good culture was obtained. Two problems: leakage at the connecting portion of a hose for supplying a liquid and 5% removal of the cell layer, occurred; however, 90% of the removed cells were alive.

Example B-1

Cell Culture Using a Cell Culture Device Having a Pressure Equalizing Mechanism (Pocket Structure)

(1) Manufacture of Reactor

A reactor was composed of a PMMA resin member with a length of 9 cm and a width of 3 cm, in which a flow channel and a cell culture section were formed, and a member used as a cover placed on the PMMA resin member. An inlet pipe and outlet pipe both having an inner diameter of 1 mm, were arranged at the side of the flow channel. Ahead of the tip of the inlet pipe, a semicircular pocket portion having a radius of 5 mm was provided in a width of 2 cm. A culture solution flow channel with a width of 2 cm and a depth of 500 µm starting from the pocket was formed. Somewhere within the flow channel, a section for placing cells with a width of 2 cm, a length of 2 cm and a depth of 1 mm was provided. Downstream of the section, a flow channel with a width of 2 cm and a depth of 500 µm was provided. Furthermore, a pocket and an outlet pipe were provided downstream of the flow channel symmetrically to those at the inlet side. To the stainless steel part (100 µm thickness, 1.98 cm width, and 1.98 cm length) for holding a water-containing polymer gel film, a gel film and cells mentioned below were attached and placed at the section for placing cells.

(2) Manufacture of Water-containing Polymer Gel Film

First, 20 g of chitosan (CT-100, manufactured by Wako Pure Chemical Industries, Ltd.) was gradually added to 1000 g of an aqueous acetic acid solution (1% by mass). The solution mixture was stirred at 40° C. for 3 hours to dissolve chitosan and filtrated through microfilter FG-30 manufactured by Fuji Photo Film Co. Ltd. The filtrated aqueous acetic acid solution of chitosan was applied by an applicator onto a polyethylene terephthalate film (200 micron of film thickness) prepared in advance to obtain a wet film of 250 micron thickness. The wet film was dried at 40° C. for 3 hours. The dried chitosan gel film was soaked in a methanol solution of sodium hydroxide (10% by mass) for 60 minutes and subsequently in a PBS solution for 60 minutes. Thereafter, the film was washed with running water for 60 minutes, dried at 40° C. for 3 hours to obtain a chitosan gel film. The chitosan gel film was sterilized by UV rays for 3 hours to obtain a water-containing polymer gel film.

(3) Culturing of Animal Cells (i) Release-type Cell Culture Film

The chitosan gel film obtained in the step (2) was soaked in a 0.1 mol/l aqueous solution of calcium chloride for 5 minutes. Thereafter, the chitosan gel film was taken out and placed on an SUS board so as not to make wrinkles. After water on the chitosan gel was absorbed by a sponge roller which was dried in advance at 40° C. for 1 hour, coating was performed by an applicator to obtain a wet film of 500 micron thickness. The coated product was soaked in a mixed aqueous solution of 0.5 mol/l calcium chloride and 0.05 mol/l 1-ethyl-3-(3-dimethylaminopropylamino)carbodiimido hydrochloride for 60 minutes, subsequently washed with running water for 30 minutes, and transferred onto a Teflon (registered trademark) plate. Thereafter, 15 g of an aqueous solution of CELLMATRIX type I-C (manufactured by Nitta gelatin) collagen (0.03% by mass) diluted with a 0.04 mol/l HEPES aqueous solution was casted and dried at 37° C. for a day and night. The film was sterilized by UV rays for 3 hours to obtain a release-type cell culture film.

(ii) Preparation of Stacked Cell Culture (a) Culture on Water-containing Polymer Gel Film Cells used: HepG2 (cells derived from human liver cancer)

Medium used: Eagle's minimum essential medium (MEM), 10% fetal bovine serum

Cell culture carrier:

The water-containing polymer gel film of the step (2) was placed in a Petri dish. A medium was added to the Petri dish, allowed to penetrate for 5 minutes, and exchanged with a fresh medium. After this procedure was repeated three times, the Petri dish was allowed to stand overnight, thereby penetrating the medium into cell culture carrier. Cells which were cultured in advance were recovered with trypsin treatment, and the cell concentration was adjusted to 50,000 cells/ml. After the cells and medium in the Petri dish were discarded, the cell solution was seeded into the Petri dish so as to obtain a cell concentration of 10,000 cells/cm$^2$ and then a medium was added. Thereafter, the Petri dish was subjected to incubation in a $CO_2$ incubator at 37° C. for 2 days.

(b) Culture on the Release-type Cell Culture Film

Cells used: BAE (bovine aorta endothelial cells)

Medium used: Eagle's minimum essential medium (MEM), 10% fetal bovine serum

Cell culture carrier:

The release-type cell culture film of the step (3)(i) was placed in a Petri dish. A medium was added to the Petri dish, allowed to penetrate for 5 minutes, and exchanged with a fresh medium. After this procedure was repeated three times, the Petri dish was allowed to stand overnight, thereby penetrating the medium into cell culture carrier. Cells which were cultured in advance were recovered with trypsin treatment, and the cell concentration was adjusted to 50,000 cells/ml. After the cells and medium in the Petri dish were discarded, the cell solution was seeded into the Petri dish so as to obtain a cell concentration of 10,000 cells/cm$^2$ and then a medium was added. Thereafter, the Petri dish was subjected to incubation in a $CO_2$ incubator at 37° C. for 2 days.

(c) Stacking of Cell Layers

On the cell culture prepared in the step (a), the cell culture prepared in the step (b) was stacked such that the cells of both cultures were in contact with each other and incubated in MEM medium overnight. The resultant cell culture was soaked in a release solution (MEM medium containing 3 mM 1-hydroxyethane-1,1-diphosphonic acid(HEDP)) for 10 minutes to dissolve a calcium alginate layer, thereby removing a nylon micro filter.

(4) Assembly of Reactor and Culturing

The cell culture of the step (3) was installed in the frame of the stainless steel part for holding a water-containing polymer gel film in the reactor of the step (1). Further, MEM (as a medium A) was supplied to the cell-layer side, and a solution containing cholic acid dissolved in an isotonic phosphate buffer (pH 7.2) at a concentration of 40 g/l (as medium B) was supplied to the opposite side of the cell layer. To simulate shearing by blood, culturing was performed by increasing the flow rate of medium A so as to apply, to the cells, a flow shearing force of 2.5 dyn/cm$^2$, which corresponds to the force shearing force at a tissue wall. As a result, good cultured cells similar to those in a living body were obtained. Release of less than 1% of the cell layer was observed in the cell culture of this Example.

Comparative Example B-1

A culture device having the same size as that described in Example B-1 (1) was used. A flow channel having an inner diameter of 1 mm was provided horizontally to a culture-solution flow channel having a width of 2 cm and a depth of 500 µm communicating to a cell culture section. The solution supplied from a pipe was spread in a fan shape by use of the pocked portion mentioned above, and fed to the culture-solution flow channel. In the cell culture device, the discharge flow channel is constructed symmetrically with respect to the cell culture section. To the stainless steel part (100 µm thickness, 1.98 cm width, and 1.98 length) for holding a water-containing polymer gel film, a gel film and cells were attached and placed at the position for cell culture section in the same manner as Example B-1. In this manner, the cell culture device of Example B-1 was prepared.

Using this cell culture device, cells were cultured in the same manner as in Example B-1, (4). When the cell culture device of Comparative Example B-1 was used, since the flow rate differs between the center portion and edge portions, flow shearing force could not be applied uniformly. When the cells were cultured by supplying a culture solution at the same flow rate as in Example B-1, release of 50% of the cell layer was observed. As a result, it was impossible to perform a culture experiment.

Example B-2

Cell Culture Using Cell Culture Device Having a Pressure Gauge and 3 Head-type Microplunger Pump (1) Manufacture of Reactor A reactor was composed of a PMMA resin member having a length of 9 cm and a width of 3 cm. The PMMA resin member was composed of two flow channel regions and a cell culture section for culturing cells sandwiched by the two flow channel regions. One of the two flow channel regions included an inlet, a pocket, and a liquid supply channel to the cell culture section. The other included a liquid discharge channel from the cell culture section, a pocket and an outlet. The flow channel region was constructed as follows. The inlet pipe was formed with an inner diameter of 1 mm. Ahead of the tip of the inlet pipe, the pocket portion, which had a semicircular shape having a radius of 5 mm, is provided at a width of 2 cm. A channel for the culture solution having a width of 2 cm was extended from this pocket portion to the pocket portion having a depth of 500 µm and a width of 2 cm at the outlet side. Downstream of the channel, the pocket and outlet pipe were provided symmetrically to those at the inlet side. The member for forming the cell culture section had a thickness of 2 mm. The gel film and cells mentioned below were attached to the stainless steel processed part (100 µm thickness, 2 cm width, and 2 cm length) for holding a water-containing polymer gel film which was arranged midway to the cell culture section, and placed at a predetermined position for the cell culture section.

(2) Manufacture of Water-containing Polymer Gel Film

First, 20 g of chitosan (CT-100, manufactured by Wako Pure Chemical Industries, Ltd.) was gradually added to 1000 g of an aqueous acetic acid solution (1% by mass). The solution mixture was stirred at 40° C. for 3 hours to dissolve chitosan and filtrated through microfilter FG-30 manufactured by Fuji Photo Film Co. Ltd. The filtrated aqueous acetic acid solution of chitosan was applied by an applicator onto a polyethylene terephthalate film (200 micron film thickness) prepared in advance to obtain a wet film of 250 micron thickness. The wet film was dried at 40° C. for 3 hours. The dried chitosan gel film was soaked in a methanol solution of sodium hydroxide (10% by mass) for 60 minutes and subsequently in a PBS solution for 60 minutes. Thereafter, the film was washed with running water for 60 minutes, dried at 40° C. for 3 hours to obtain a chitosan gel film. The chitosan gel film was sterilized by UV rays for 3 hours to obtain a water-containing polymer gel film.

(3) Culturing of Animal Cells (i) Release-type Cell Culture Film

The chitosan gel film obtained in the step (2) was soaked in an aqueous solution of calcium chloride (0.1 mol/l) for 5 minutes. Thereafter, the chitosan gel film was taken out and placed on an SUS board so as not to make wrinkles. After water on the chitosan gel was absorbed by a sponge roller which was dried in advance at 40° C. for 1 hour, coating was performed by an applicator to obtain a wet film of 500 micron thickness. The coated product was soaked in a mixed aqueous solution of 0.5 mol/l calcium chloride and 0.05 mol/l 1-ethyl-3-(3-dimethylaminopropylamino)carbodiimido hydrochloride for 60 minutes, subsequently washed with running water for 30 minutes, and transferred onto a Teflon (registered trademark) plate. Thereafter, 15 g of an aqueous solution of CELLMATRIX type I-C (manufactured by Nitta gelatin) collagen (0.03% by mass) diluted with 0.04 mol/l HEPES aqueous solution was casted and dried at 37° C. for a day and night. The film was sterilized by UV rays for 3 hours to obtain a release-type cell culture film.

(ii) Preparation of Stacked Cell Culture (a) Culture on Water-containing Polymer Gel Film Cells used: HepG2 (cells derived from human liver cancer)

Medium used: Eagle's minimum essential medium (MEM), 10% fetal bovine serum

Cell culture carrier:

The water-containing polymer gel film of the step (2) was placed in a Petri dish. A medium was added to the Petri dish, allowed to penetrate for 5 minutes, and exchanged with a fresh medium. After this procedure was repeated three times, the Petri dish was allowed to stand overnight, thereby penetrating the medium into cell culture carrier. Cells which were cultured in advance were recovered with trypsin treatment and the cell concentration was adjusted to 50,000 cells/ml. After the cells and medium in the Petri dish were discarded, the cell solution was seeded so as to obtain a cell concentration of 10,000 cells/cm$^2$ and then a medium was added. Thereafter, the Petri dish was subjected to incubation in a $CO_2$ incubator at 37° C. for 2 days.

(b) Culture on the Release-type Cell Culture Film

Cells used: BAE (bovine aorta endothelial cells)

Medium used: Eagle's minimum essential medium (MEM), 10% fetal bovine serum

Cell culture carrier:

The release-type cell culture film of the step (3)(i) was placed in a Petri dish. A medium was added to the Petri dish, allowed to penetrate for 5 minutes, and exchanged with a fresh medium. After this procedure was repeated three times, the Petri dish was allowed to stand overnight, thereby penetrating the medium into cell culture carrier. Cells which were cultured in advance were recovered with trypsin treatment and the cell concentration was adjusted to 50,000 cells/ml. After the cells and medium in the Petri dish were discarded, the cell solution was seeded in a Petri dish so as to obtain a cell concentration of 10,000 cells/cm$^2$ and then a medium was added. Thereafter, the Petri dish was subjected to incubation in a $CO_2$ incubator at 37° C. for 2 days.

(c) Stacking of Cell Layers

On the cell culture prepared in the step (a), the cell culture prepared in the step (b) was stacked such that the cells of both cultures were in contact with each other and incubated in MEM medium overnight. The resultant cell culture was soaked in a release solution (MEM medium containing 3 mM 1-hydroxyethane-1,1-diphosphonic acid(HEDP)) for 10 minutes to dissolve a calcium alginate layer, thereby removing a nylon micro filter.

(4) Assembly of Reactor and Culturing

The cell culture of the step (3) was installed in the frame of the stainless steel part for holding a water-containing polymer gel film in the cell culture device of the step (1). Further, MEM (as a medium A) was supplied to the cell-layer side and a solution containing cholic acid dissolved in an isotonic phosphate buffer (pH 7.2) at a concentration of 40 g/L (as medium B) was supplied to the opposite side of the cell layer. To simulate shearing by blood, the flow rate of medium A was controlled so as to apply, to the cells, a flow shearing force of 2.5 dyn/cm$^2$, which corresponds to the flow shearing force at a tissue wall. At this time, the pressure was measured by a pressure gauge attached to the pocket portion at the inlet side. It was 0.1 MPa in average. This pressure value was set as a target pressure. Culturing was performed while controlling the flow rate of three-head type microplunger pump (used as a feed pump) so as to render the pressure constant at the target pressure value. As a result, good cultured cells similar to those obtained in a living body were obtained. At this time, the change in pressure when a head was switched was improved to 1.2%. The change in pressure during steady operation time was 1.0%. In the culture of this embodiment, release of less than 1% of the cell layer was observed.

Comparative Example B-2

By using the same device as in Example B-2 and using a three-head type microplunger pump as a liquid supply pump for supplying a liquid to a culture section, long-time continuous operation was successfully performed. In this case, a change in flow amount when a head was switched was 5% of that during the steady operation time. A change in pressure was 3.9% of that during the steady operation time. The pulsation rate of the flow was 1.1% and a pressure change was 0.9% during steady operation time.

Using this culture device, cells were cultured in the same manner as in Example B-2. In the comparative example, release of 21% of the cell layer was observed due to pressure change taking place when three heads were changed.

Example B-3

Cell Culturing Using a Cell Culture Device Having a Pressure Change Absorbing Unit (Gas Chamber)

(1) Manufacture of Reactor

A reactor was composed of a PMMA resin member of 9 cm length and 3 cm width. The PMMA resin member was composed of two flow channel regions and a cell culture section for culturing cells sandwiched by the two flow channel regions. One of the two flow channel regions included an inlet, a pocket, and a liquid supply channel to the cell culture section. The other included a liquid discharge channel from the cell culture section, a pocket and an outlet. The flow channel region was constructed as follows. The inlet pipe was formed with an inner diameter of 1 mm. Ahead of the tip of the inlet pipe, the pocket portion, which had a semicircular shape having a radius of 5 mm, is provided at a width of 2 cm. The liquid channel having 2 cm width and 500 μm depth was extended from this pocket portion to the pocket portion of 2 cm width at the outlet side. Downstream of the liquid channel, the pocket and outlet pipe were provided symmetrically to those at the inlet side. The member for forming the cell culture section had a thickness of 2 mm. The gel film and cells mentioned below were attached to the stainless steel processed part (100 μm thickness, 2 cm width, and 2 cm length) for holding a water-containing polymer gel film, which was arranged within the cell culture section, and placed at a predetermined position for the cell culture section.

(2) Manufacture of Water-containing Polymer Gel Film

First, 20 g of chitosan (CT-100, manufactured by Wako Pure Chemical Industries, Ltd.) was gradually added to 1000 g of an aqueous acetic acid solution (1% by mass). The solution mixture was stirred at 40° C. for 3 hours to dissolve chitosan and filtrated through microfilter FG-30 manufactured by Fuji Photo Film Co. Ltd. The filtrated aqueous acetic acid solution of chitosan was applied by an applicator onto a polyethylene terephthalate film (200 micron film thickness) prepared in advance to obtain a wet film of 250 micron thickness. The wet film was dried at 40° C. for 3 hours. The dried chitosan gel film was soaked in a methanol solution of sodium hydroxide (10% by mass) for 60 minutes and subsequently in a PBS solution for 60 minutes. Thereafter, the film was washed with running water for 60 minutes, dried at 40° C. for 3 hours to obtain a chitosan gel film. The chitosan gel film was sterilized by UV rays for 3 hours to obtain a water-containing polymer gel film.

(3) Culturing of Animal Cells (i) Release-type Cell Culture Film

The chitosan gel film obtained in the step (2) was soaked in an aqueous solution of calcium chloride (0.1 mol/l) for 5 minutes. Thereafter, the chitosan gel film was taken out and placed on an SUS board so as not to make wrinkles. After water on the chitosan gel was absorbed by a sponge roller which was dried in advance at 40° C. for 1 hour, coating was performed by an applicator to obtain a wet film of 500 micron thickness. The coated product was soaked in a mixed aqueous solution of 0.5 mol/l calcium chloride and 0.05 mol/l 1-ethyl-3-(3-dimethylaminopropylamino)carbodiimido hydrochloride for 60 minutes, subsequently washed with running water for 30 minutes, and transferred onto a Teflon (registered trademark) plate. Thereafter, 15 g of an aqueous solution of CELLMATRIX type I-C (manufactured by Nitta gelatin) collagen (0.03% by mass) diluted with a 0.04 mol/l HEPES aqueous solution was casted and dried at 37° C. for a day and night. The film was sterilized by UV rays for 3 hours to obtain a release-type cell culture film.

(ii) Preparation of Stacked Cell Culture (a) Culturing on Water-containing Polymer Gel Film Cells used: HepG2 (cells derived from human liver cancer)

Medium used: Eagle's minimum essential medium (MEM), 10% fetal bovine serum

Cell culture carrier:

The water-containing polymer gel film of the step (2) was placed in a Petri dish. A medium was added to the Petri dish, allowed to penetrate for 5 minutes, and exchanged with a fresh medium. After this procedure was repeated three times, the Petri dish was allowed to stand overnight, thereby penetrating the medium into cell culture carrier. Cells which were cultured in advance were recovered with trypsin treatment and the cell concentration was adjusted to 50,000 cells/ml. After the cells and medium in the Petri dish were discarded, the cell solution was seeded in a Petri dish so as to obtain a cell concentration of 10,000 cells/cm$^2$ and then a medium was added. Thereafter, the Petri dish was subjected to incubation in a $CO_2$ incubator at 37° C. for 2 days.

(b) Culture on the Release-type Cell Culture Film

Cells used: BAE (bovine aorta endothelial cells)

Medium used: Eagle's minimum essential medium (MEM), 10% fetal bovine serum

Cell culture carrier:

The release-type cell culture film of the step (3)(i) was placed in a Petri dish. A medium was added to the Petri dish, allowed to penetrate for 5 minutes, and exchanged with a fresh medium. After this procedure was repeated three times, the Petri dish was allowed to stand overnight, thereby penetrating the medium into cell culture carrier. Cells which were cultured in advance were recovered with trypsin treatment and the cell concentration was adjusted to 50,000 cells/ml. After the cells and medium in the Petri dish were discarded, the cell solution was seeded in a Petri dish so as to obtain a cell concentration of 10,000 cells/cm$^2$ and then a medium was added. Thereafter, the Petri dish was subjected to incubation in a $CO_2$ incubator at 37° C. for 2 days.

(c) Stacking of Cell Layers

On the cell culture prepared in the step (a), the cell culture prepared in the step (b) was stacked such that the cells of both cultures were in contact with each other and incubated in MEM medium overnight. The resultant cell culture was soaked in a release solution (MEM medium containing 3 mM 1-hydroxyethane-1,1-diphosphonic acid(HEDP)) for 10 minutes to dissolve a calcium alginate layer, thereby removing a nylon micro filter.

(4) Assembly of Reactor and Culturing

The cell culture of the step (3) was installed in the frame of the stainless steel part for holding a water-containing polymer gel film in the cell culture device of the step (1). Further, MEM (as a medium A) was supplied to the cell-layer side and a solution containing cholic acid dissolved in an isotonic phosphate buffer (pH 7.2) at a concentration of 40 g/l (as medium B) was supplied to the opposite side of the cell layer. To simulate shearing by blood, the flow rate of medium A was controlled so as to apply, to the cells, a flow shearing force of 2.5 dyn/cm$^2$, which corresponds to the flow shearing force at a tissue wall. At this time, since there was no appropriate flow meter, a change in flow rate at the inlet of the culture device was obtained as follows. The ratio of the range of fluctuation of pressure to the entire pressure was obtained by the semiconductor pressure gauge and the ratio was defined as a pulsation value. According to this definition, actual liquid supply conditions were analyzed, and a pulsation value of 1.5% was obtained. Similarly, based on the measurement at a gas chamber above the pocket near the inlet of the culture device, the pulsation rate was greatly lowered to 0.2%. Cells were cultured successfully by the method of this embodiment, and release of cells was rarely observed.

Comparative Example B-3

By using the same device as in Example B-3 and using a three-head type microplunger pump as a liquid supply pump for supplying a liquid to a culture section, long-time continuous operation was successfully performed. In this case, a change in flow amount when a head was switched was 4.5% of that during the steady operation time. A change in pressure was 3.6% of that during the steady operation time. The pulsation rate of the flow was 1.0% and a pressure change was 0.9% during steady operation time.

In this comparative example, the pulsation ratio was determined by a pressure gauge attached to the upper portion of the pocket at the inlet side. As a result, the pulsation ratio was 0.6%. Cells were cultured successfully; however, it was confirmed that the cell release ratio was 2%.

Example C-1

(1) Manufacture of Reactor

A reactor was composed of a PMMA resin member of 9 cm length and 3 cm width. The PMMA resin member was composed of two flow channel regions and a cell culture section for culturing cells sandwiched by the two flow channel regions. One of the two flow channel regions included an inlet, a pocket, and a liquid supply channel to the cell culture section. The other included a liquid discharge channel from the cell culture section, a pocket and an outlet. The flow channel region was constructed as follows. The inlet pipe was formed with an inner diameter of 1 mm. Ahead of the tip of the inlet pipe, the pocket portion, which had a semicircular shape having a radius of 5 mm, is provided at a width of 2 cm. The liquid supply channel having 2 cm width and 500 µm depth was extended from this pocket portion to the pocket portion of 2 cm width at the outlet side. Downstream of the liquid channel, the pocket and outlet pipe were provided symmetrically to those of the inlet side. Peltier type temperature control devices having a width of 2.1 cm and a length of 2.5 cm were provided under the liquid supply channel and liquid discharge channel (with a thickness of 1 mm). Furthermore, another Peltier type temperature control device having a width of 2 cm and a length of 2 cm was provided immediately under the cell culture section. A vacuum heat insulating sections of 2.8 cm width and 2 mm length were provided every between the adjacent temperature control devices. The member for forming the cell culture section had a thickness of 2 mm. The gel film and cells mentioned below were attached to the stainless steel processed part (100 µm thickness, 2 cm width, and 2 cm length) for holding a water-containing polymer gel film, which was arranged within the cell culture section, and placed at a predetermined position for the cell culture section.

(2) Temperature Measurement

Particles (average particle diameter: 5 µm) having a microcapsulated temperature sensitive liquid crystal (visual recognition was made when temperature changed by ±1° C.) were prepared. The particles were dispersed in the liquid to be used as a sample. The temperature of the liquid to be supplied was set at 20° C. and the temperature of a cell culture section was set at 30° C. The liquid supply channel to the cell culture section was heated to 31.5° C. such that the temperature of the liquid of 20° C. was raised to 30° C. just upstream of the cell culture section at the time it was introduced to the cell culture section. To set the temperature of the liquid flowing out from the cell culture section at 25°

C., the liquid was exposed to 24.3° C. and cool. It was confirmed that the color of the liquid flowing through the culture device becomes uniform in the width direction, and that the temperature was controlled such that the liquid exhibited the same colors as those previously observed at individual temperatures as measured by a thermometer.

(3) Manufacture of Water-containing Polymer Gel Film

First, 20 g of chitosan (CT-100, manufactured by Wako Pure Chemical Industries, Ltd.) was gradually added to 1000 g of an aqueous acetic acid solution (1% by mass). The solution mixture was stirred at 40° C. for 3 hours to dissolve chitosan and filtrated through microfilter FG-30 manufactured by Fuji Photo Film Co. Ltd. The filtrated aqueous acetic acid solution of chitosan was applied by an applicator onto a polyethylene terephthalate film (200 micron in film thickness) prepared in advance to obtain a wet film of 250 micron thickness. The wet film was dried at 40° C. for 3 hours. The dried chitosan film was soaked in a methanol solution of sodium hydroxide (10% by mass) for 60 minutes and subsequently in a PBS solution for 60 minutes. Thereafter, the film was washed with running water for 60 minutes, dried at 40° C. for 3 hours to obtain a chitosan gel film. The chitosan gel film was sterilized by UV rays for 3 hours to obtain a water-containing polymer gel film.

(4) Culturing of Animal Cells (i) Release-type Cell Culture Film

The chitosan gel film obtained in the step (2) was soaked in an aqueous solution of calcium chloride (0.1 mol/l) for 5 minutes. Thereafter, the chitosan gel film was taken out and placed on an SUS board so as not to make wrinkles. After water on the chitosan gel was absorbed by a sponge roller which was dried in advance at 40° C. for 1 hour, coating was performed by an applicator to obtain a wet film of 500 micron thickness. The coated product was soaked in a mixed aqueous solution of 0.5 mol/l calcium chloride and 0.05 mol/l 1-ethyl-3-(3-dimethylaminopropylamino)carbodiimido hydrochloride for 60 minutes, subsequently washed with running water for 30 minutes, and transferred onto a Teflon (registered trademark) plate. Thereafter, 15 g of an aqueous solution of CELLMATRIX type I-C (manufactured by Nitta Gelatin Inc.) collagen (0.03% by mass) diluted with a 0.04 mol/l HEPES aqueous solution was casted and dried at 37° C. for a day and night. The film was sterilized by UV rays for 3 hours to obtain a release-type cell culture film.

(ii) Preparation of Stacked Cell Culture (a) Culturing on Water-containing Polymer Gel Film Cells used: HepG2 (cells derived from human liver cancer)

Medium used: Eagle's minimum essential medium (MEM), 10% fetal bovine serum

Cell culture carrier:

The water-containing polymer gel film of the step (3) was placed in a Petri dish. A medium was added to the Petri dish, allowed to penetrate for 5 minutes, and exchanged with a fresh medium. After this procedure was repeated three times, the Petri dish was allowed to stand overnight, thereby penetrating the medium into cell culture carrier. Cells which were cultured in advance were recovered with trypsin treatment and the cell concentration was adjusted to 50,000 cells/ml. After the cells and medium in the Petri dish were discarded, the cell solution was seeded in a Petri dish so as to obtain a cell concentration of 10,000 cells/$cm^2$ and then a medium was added. Thereafter, the Petri dish was subjected to incubation in a $CO_2$ incubator at 37° C. for 2 days.

(b) Culturing on the Release-type Cell Culture Film

Cells used: BAE (bovine aorta endothelial cells)

Medium used: Eagle's minimum essential medium (MEM), 10% fetal bovine serum

Cell culture carrier:

The release-type cell culture film of the step (i) was placed in a Petri dish. A medium was added to the Petri dish, allowed to penetrate for 5 minutes, and exchanged with a fresh medium. After this procedure was repeated three times, the Petri dish was allowed to stand overnight, thereby penetrating the medium into cell culture carrier. Cells which were cultured in advance were recovered with trypsin treatment and the cell concentration was adjusted to 50,000 cells/ml. After the cells and medium in the Petri dish were discarded, the cell solution was seeded in a Petri dish so as to obtain a cell concentration of 10,000 cells/$cm^2$ and then a medium was added. Thereafter, the Petri dish was subjected to incubation in a $CO_2$ incubator at 37° C. for 2 days.

(c) Stacking of Cell Layers

On the cell culture prepared in the step (a), the cell culture prepared in the step (b) was stacked such that the cells of both cultures were in contact with each other and incubated in MEM medium overnight. The resultant cell culture was soaked in a release solution (MEM medium containing 3 mM 1-hydroxyethane-1,1-diphosphonic acid (HEDP)) for 10 minutes to dissolve a calcium alginate layer, thereby removing a nylon micro filter.

(5) Assembly of Reactor and Culturing

The cell culture of the step (4) was installed in the frame of the stainless steel part for holding a water-containing polymer gel film in the reactor of the step (1). Further, MEM (as a medium A) was supplied to the cell-layer side and a solution containing cholic acid dissolved in an isotonic phosphate buffer (pH 7.2) at a concentration of 40 g/l (as medium B) was supplied to the opposite side of the cell layer. To simulate shearing by blood, the flow rate of medium A was adjusted so as to apply, to the cells, a flow shearing force of 2.5 dyn/$cm^2$, which corresponds to the flow shearing force at a tissue wall. Further, the following system was constructed. The temperature of a mother liquid was set at 20° C., the temperature of the culture section was set at 25° C., the liquid to be supplied to the culture section was heated by a Peltier element to 25° C., and the liquid discharged from the culture section was cooled by another Peltier element to 20° C. Then, test culturing was performed for 72 hours. In this case, thermocouples were attached to the inlet-side pocket, outlet-side pocket, and the cell culture section to continuously monitor a positive temperature change, thereby evaluating the stability of temperature control. As a result, the temperature was quite stably controlled within 2.5±° C. Furthermore, cell culturing was successively performed by the method of this embodiment, and virtually no release of cells was observed.

Comparative Example C

In Comparative example C, a reactor was manufactured in the same manner as in Example C-1 (1) except that a Peltier-type temperature control device and a vacuum heat insulating section were not provided. Cells were cultured while keeping the room temperature at 20° C.

In the case of Comparative Example C, the pulsation rate was measured by a pressure gauge attached above the pocket at the inlet side. As a result, the pulsation ratio was 0.6%. Cells were cultured successfully. However, release of 1% or less of cells was observed.

Example D-1

A reactor was composed of a PMMA resin member of 9 cm length and 3 cm width. The PMMA resin member was composed of two flow channel regions and a cell culture section for culturing cells sandwiched by the two flow channel regions. One of the two flow channel regions included an inlet, a pocket, and a liquid supply channel to the cell culture section. The other included a liquid discharge channel from the cell culture section, a pocket and an outlet. The flow channel region was constructed as follows. The inlet pipe was formed with an inner diameter of 1 mm. Ahead of the tip of the inlet pipe, the pocket portion, which had a semicircular shape having a radius of 5 mm, is provided at a width of 2 cm. The liquid channel having 2 cm width and 500 μm depth was extended from this pocket portion to the pocket portion of 2 cm width at the outlet side. Downstream of the liquid channel, pocket and outlet pipe were provided symmetrically to those of the inlet side. The member for forming the cell culture section had a thickness of 2 mm. The gel film and cells mentioned below were attached to the stainless steel processed part (100 μm thickness, 2 cm width, and 2 cm length) for holding a water-containing polymer gel film, which was arranged within the cell culture section, and placed at a predetermined position to prepare the cell culture devise. Upstream of the cell culture devise, a mass flowmeter (manufactured by Sakura Endless) was attached. Further upstream of the mass flowmeter, a raw material supply tank of 5 L volume was arranged. 3 L of a culture solution was placed therein, and a liquid (culture solution) was supplied by pressuring the tank while controlling the flow rate by a servo valve (manufactured by Tokyo Seimitsu Co., Ltd.) such that the liquid (culture solution) was supplied at a flow rate of 100 ml/min. Upstream of the raw material supply tank, a raw material preparation tank was arranged. When the liquid level of the raw material supply tank reached 1.5 L, 3.5 L of the liquid was supplied at a flow rate of 1 L/min by a gear pump (manufacture d by MAAG).

A change in flow rate measured by flowmeter during a steady operation time was 0.48%. A momentary change when a liquid was transferred from the raw material preparation tank to the raw material supply tank was 0.8%. A change in flow rate during transfer of the liquid was 0.55%. A change in flow rate at the time liquid transfer was completed, was 0.72%. As described, the flow rate was controlled quite accurately. No release of cells was observed.

Comparative Example D-1

A reactor was manufactured by using the same device as in Example D-1 and a three-head type microplunger pump was used as the liquid supply pump for supplying a liquid to a cell culture section to attain a long-time continuous operation. In this case, a change in flow rate when a head was switched was 4.5% of the flow rate during a steady operation. A pressure change was 3.6% of that during the steady operation. A flow pulsation rate during the steady operation was 1.0%, and a pressure change during the steady operation was 0.9%.

In the case of Comparative Example D-1, when a pulsation rate was measured by the pressure gauge attached above the pocket at the inlet side, it was 0.6%. Cells were successively cultured; however, release of 2% of cells was observed.

ADVANTAGES OF THE INVENTION

By using the cell culture device of the present invention, animal cells can be cultured while supplying different liquid mediums to both surfaces of the cells. In addition, since the medium in contact with the animal cells can realize the shearing and the substance supply in the same way as blood does, cells can be cultured in living-body analogous conditions while preventing a cell layer from being released.

The cell culture system is very sensitive. The structure of a culture device and the operational conditions have a large effect on the culturing. The present inventors have focused attention to the structure of a culture device, in particular, to the flow therein, and they realized culturing while preventing cell death and release of cells by attaining uniform flow in the culture device. In the present invention, to supply a desired liquid stably for a long time, a means for suppressing a pressure change at the time of switching a liquid feed means was employed, thereby preventing release of cells and stabilizing an experiment system.

According to the present invention, it is further possible to attain long-time stable supply of a liquid to a cell culture system with a high accuracy by a quite simple and convenient pump. More specifically, when culture is performed for a long time, an uneven flow is caused by small air bubbles present in a liquid and/or a flow channel from a tank to a culture unit, since the bubbles deposited and stored in a culture section and/or a pocket section interfere with a flow. To deal with this problem, a gas chamber is provided to trap bubbles above the pocket at the inlet side. In this manner, a very stable operation is achieved.

Moreover, the cell culture device of the present invention makes it possible to stably control the temperature uniform in a flow direction and a width direction for a long time. According to the present invention, to realize cell culture tests and cell metabolism tests which will be increasingly required from now on, it is possible to provide a practical device having a temperature control unit installed therein.

When cells are cultured, various limitations are imposed on raw materials to be used, rendering construction of a system difficult. However, stable and long-time cell culture while maintaining accuracy can be realized by using the cell culture device of the present invention.

The invention claimed is:

1. A device for culturing cells which comprises:
   at least one water-containing polymer gel film for adhering animal cells onto at least one surface of the film,
   a structure capable of supplying different liquids to both sides of the film wherein the structure comprises at least one flow channel, formed by the water-containing gel film and an inner wall of a reactor, for supplying a culture solution to a cell culture section having a uniform width, and
   a means for holding the water-containing polymer gel film between the flow channels,
   wherein a pocket structure is provided for establishing a uniform dynamic pressure of the culture solution across the uniform width while culture solution is introduced through an inlet pipe, so as to establish a uniform flow rate by applying a flow shearing force to the animal cells.

2. The device according to claim 1, wherein the at least one flow channels is provided on one and the other sides of the water-containing polymer gel film in such a way that the different liquids can flow to one and the other sides of the film.

3. The device according to claim 1, which comprises at least one water-containing polymer gel film for adhering animal cells onto at least one surface of the film, at least one flow channels provided on one and the other sides of the water-containing polymer gel film in such a way that different liquids can flow to one and the other side of the film, and a means for holding the water-containing polymer gel film between the flow channels.

4. The device according to claim 1, wherein one surface of the water-containing polymer gel film is covered with an animal cell adhesive material.

5. The device according to claim 1, wherein the flow shearing force applied to the cells is at least 2.0 dyn/cm$^2$.

6. The device according to claim 1, wherein the at least one flow channels is formed of the water-containing polymer gel film and an inner wall of the reactor, and the spacing between the water-containing polymer gel film and the inner wall of the reactor falls within 10 μm to 2 mm, both inclusive.

7. The device according to claim 1, wherein 90% to 100% region, both inclusive, of the surface of the water-containing polymer gel film is coated with the animal cells which are adhered to the film.

8. The device according to claim 1, wherein the water-containing polymer gel film contains chitosan.

9. The device according to claim 1, wherein the water-containing polymer gel film has a dry film thickness of 5 μm to 200 μm, both inclusive.

10. The device according to claim 1, wherein 2 to 10 types of animal cells are used as the animal cells.

11. The device according to claim 1, wherein the animal cells are stacked in 2 to 10 layers.

12. A method of culturing animal cells, which comprises supplying different liquids to one and the other sides of a water-containing polymer gel film having animal cells adhered onto at least one of the surfaces thereof by using the device according to claim 1.

* * * * *